(12) United States Patent
Liu et al.

(10) Patent No.: US 7,186,681 B2
(45) Date of Patent: Mar. 6, 2007

(54) METHODS OF MODULATING CELL MIGRATION USING GALECTIN-3

(75) Inventors: Fu-Tong Liu, San Diego, CA (US);
Hideki Sano, San Diego, CA (US);
Daniel K. Hsu, San Diego, CA (US)

(73) Assignee: La Jolla Institute for Allergy and Immunology, San Diego, CA (US)

( * ) Notice: Subject to any disclaimer, the term of this patent is extended or adjusted under 35 U.S.C. 154(b) by 779 days.

(21) Appl. No.: 09/805,449

(22) Filed: Mar. 13, 2001

(65) Prior Publication Data

US 2002/0044932 A1    Apr. 18, 2002

Related U.S. Application Data

(60) Provisional application No. 60/188,795, filed on Mar. 13, 2000.

(51) Int. Cl.
*A01N 37/18*    (2006.01)
*A61K 38/00*    (2006.01)
*A61K 39/395*   (2006.01)

(52) U.S. Cl. ........................ 514/2; 424/143.2
(58) Field of Classification Search ................ 435/7.2; 514/2
See application file for complete search history.

(56) References Cited

U.S. PATENT DOCUMENTS 5,869,289 A * 2/1999 Hawkins et al.

OTHER PUBLICATIONS

Hughes RC. Glycobiology 4(1):5-12, 1994.*
Nangia-Makker et al.; Galectin-3 Induces Endothelial Cell Morphogenesis and Angiogenesis; American Journal of Pathology, vol. 156, No. 3; Mar. 2000; pp; 899-909.
Yang et al.; Expression of galectin-3 modulates T-cell growth and apoptosis, Proc. Natl. Acad. Sci. USA, vol 93; Jun. 1996; pp. 6737-6742.
Frigeri et al.; εBP, a β-Gelactoside-Binding Animal Lectin, Recognizes IgE Receptor (FcεRI) and Activates Mast Cells; Biochemistry, vol. 32; No. 30: 1993;pp. 7644-7649.

* cited by examiner

*Primary Examiner*—Robert S. Landsman
(74) *Attorney, Agent, or Firm*—Pillsbury Winthrop Shaw Pittman LLP

(57) ABSTRACT

The present invention relates to methods of modulating cell migration, particularly, monocyte, neutrophil or macrophage migration, using galectin-3, galectin-3 binding polypeptide, or galectin-3 receptor binding polypeptide. Specifically provided are methods for increasing cell migration to sites of inflammation, infection or a tumor. Also provided are methods for identifying agents that modulate galectin-3 mediated migration, compositions containing galectin-3 or a functional subsequence thereof, and microfabricated devices that deliver galectin-3 or functional galectin-3 subsequences.

21 Claims, 12 Drawing Sheets

METHODS OF MODULATING CELL MIGRATION USING GALECTIN-3

CROSS REFERENCE TO RELATED APPLICATIONS

This application is based on Provisional Application Ser. No. 60/188,795, which was filed on Mar. 13, 2000, and priority is claimed thereto.

STATEMENT AS TO FEDERALLY SPONSORED RESEARCH

This work was supported in part by National Institute of Health Grant No. RO1 AI39620. The government may have certain rights in the invention.

FIELD OF THE INVENTION

The present invention relates to methods for modulating migration of cells, especially monocytes, neutrophils and macrophages, using galectin-3, galectin-3 binding polypeptides, galectin-3 receptor binding polypeptides or galectin-3 mimetics. The invention also relates to screening methods for identifying agents that modulate galectin-3-mediated cell migration.

BACKGROUND OF THE INVENTION

Lectins are proteins that bind to specific carbohydrate structures and can thus recognize particular glycoconjugates. Galectins are a family of over 10 structurally related lectins that bind beta-galactosides.

Galectin-3 is a 26 kDa beta-galactoside-binding protein belonging to the galectin family. This protein is composed of a carboxyl-terminal carbohydrate-recognition domain (CRD) and amino-terminal tandem repeats. Galectin-3 is found in epithelia of many organs, as well as in various inflammatory cells, including macrophages, dendritic cells and Kupffer cells. The expression of galectin-3 is upregulated during inflammation, cell proliferation, cell differentiation, and through transactivation by viral proteins. Its expression is also affected by neoplastic transformation—upregulated in certain types of lymphomas and thyroid carcinoma; downregulated in other types of malignancies, such as colon, breast, ovarian and uterine carcinomas. Recently, it has been reported that the expression of this lectin has a strong correlation with the grade and malignant potential of primary brain tumors. Increased galectin-3 expression has also been noted in human atherosclerotic lesions. These findings suggest that galectin-3 may mediate both physiological and pathological responses.

Galectin-3 has been shown to function through both intracellular and extracellular actions. Related to its intracellular functions, galectin-3 has been identified as a component of hnRNP, a factor in pre-mRNA splicing. Intracellular galectin-3 has also been found to exert cell cycle control and prevent T cell apoptosis, the latter probably mediated through interaction with the Bcl-2 family members. Extracellular forms of galectin-3 secreted from monocytes/macrophages and epithelial cells, function in the activation of various types of cells, including monocytes/macrophages, mast cells, neutrophils, and lymphocytes. Galectin-3 has also been shown to mediate cell-cell and cell-extracellular matrix interactions.

Galectin-9, another member of the galectin family with two CRDs, is a selective chemoattractant for eosinophils. The activity requires both CRDs, suggesting that cross-linking of cell surface molecules is involved in the chemoattraction. Galectin-3 is known to form dimers through the amino-terminal non-lectin domain and thus has the potential to cross-link appropriate cell surface glycoproteins.

Extracellularly, galectin-3 is known to bind to the cell surfaces of monocytes/macrophages. High levels of galectin-3 expression are seen in human and rat lungs, where macrophages are one of the dominant cell types. Moreover, the recruitment of macrophages during peritonitis has been found to be attenuated in galectin-3-deficient mouse.

SUMMARY OF THE INVENTION

The present invention provides a method for modulating migration of a cell that expresses a galectin-3 receptor comprising contacting the cell with a migration-modulating amount of galectin-3, galectin-3 binding polypeptide, or galectin-3 receptor binding polypeptide.

Also provided is a method for modulating monocyte, neutrophil or macrophage migration comprising contacting a monocyte or macrophage with a migration-modulating amount of galectin-3, galectin-3 binding polypeptide, or galectin-3 receptor binding polypeptide.

According to these methods, the migration may be stimulated or inhibited. Further, the galectin-3 may comprise an N-terminal or C-terminal subsequence of galectin-3, while the galectin-3 binding polypeptide may be a galectin-3 antibody or binding fragment thereof. Preferably, migration is modulated in an animal.

The present invention also provides methods for increasing migration of monocytes, neutrophils or macrophages to an inflammatory, infection or tumor site comprising contacting the inflammatory, infection or tumor site, respectively, with a migration-increasing amount of galectin-3, galectin-3 binding polypeptide, or galectin-3 receptor binding polypeptide.

In one embodiment, the invention provides a method for identifying an agent that modulates galectin-3 mediated cell migration comprising: contacting galectin-3 with a test agent; and detecting galectin-3 mediated cell migration, wherein an alteration of galectin-3 meditated cell migration in the presence of the test agent identifies an agent that modulates galectin-3 mediated cell migration. The agent may increase or decrease galectin-3 mediated cell migration, and may be, for example, a small molecule. Contacting according to this method may be in vitro, in cells or in vivo.

Also provided by the invention is an antibody that specifically binds galectin-3. Compositions comprising galectin-3 or a functional subsequence thereof and a pharmaceutically acceptable carrier, excipient or diluent or a drug are encompassed by the invention. The drug can, for example, be an anti-tumor, antiviral, antibacterial, anti-mycobacterial, anti-fungal, anti-cell proliferative or apoptotic agent.

Also included is a composition comprising galectin-3 or a functional subsequence thereof and an article of manufacture. The article of manufacture can be a dressing, such as a bandage, a suture, a sponge, or a surgical dressing.

The present invention also includes a microfabricated device containing galectin-3 or a functional subsequence thereof in a pharmaceutically acceptable carrier, said device capable of controlled delivery of the galectin-3 or the functional subsequence. According to this embodiment of the invention, the device can be implanted in the body of a subject at site of infection, in close proximity to or within a solid tumor, or at a site of a lesion.

DETAILED DESCRIPTION OF THE INVENTION

Figure 1:
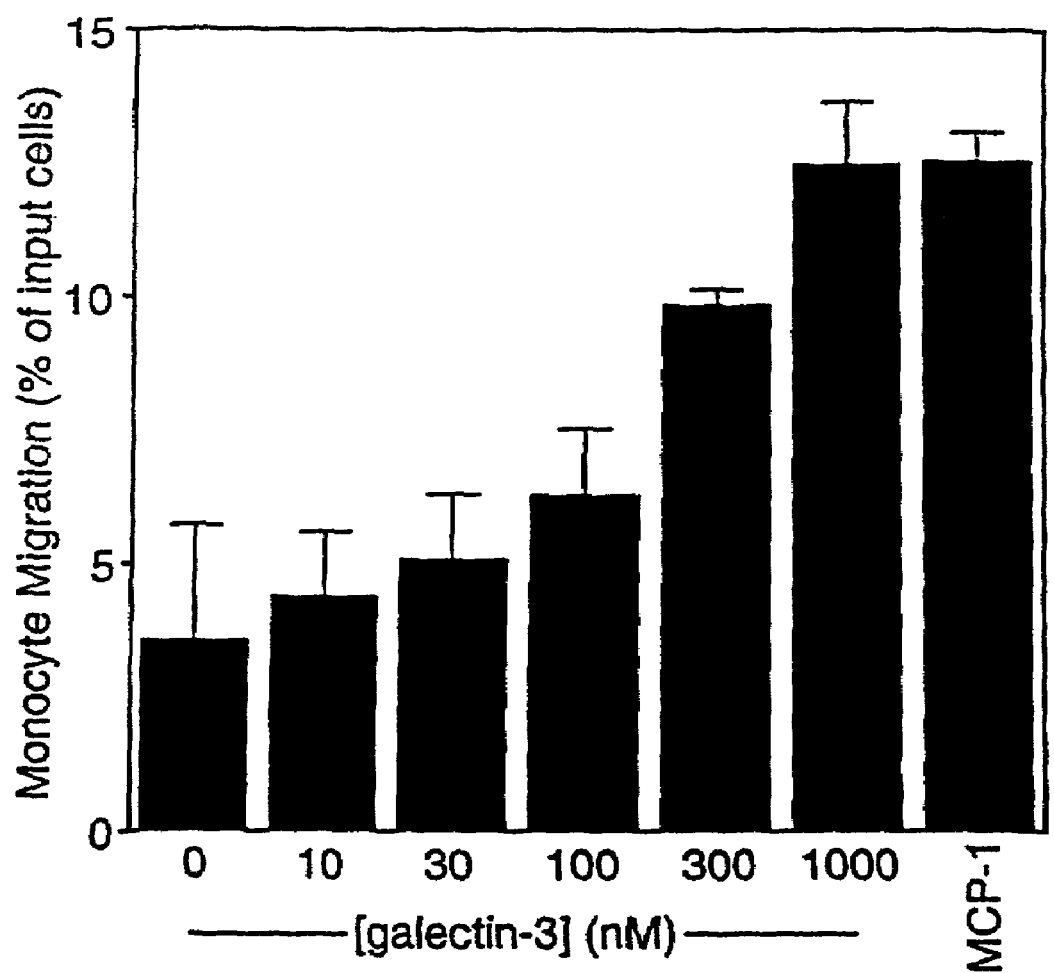
FIG. 1 shows the effect of galectin-3 on human peripheral blood monocyte migration in vitro. Various concentrations of galectin-3 [and MCP-1 (100 ng/ml) as a positive control] were applied to the lower chambers of a micro Boyden chamber, purified monocytes were applied to the upper chambers, and the migration assay was performed. Methods. Data are the mean±SD of 4 individual experiments.

The present invention is based on the observation that galectin-3 acts as chemoattractant for monocytes and macrophages. As used herein, "chemoattractant" refers to a substance that elicits accumulation of cells. Similar to many chemoattractants, galectin-3 causes a $Ca^{2+}$ influx in monocytes and both the chemotactic effect and the induction of $Ca^{2+}$ influx involve PTX-sensitive pathway(s). However, cross-desensitization experiments suggest that the signaling pathway(s) appears to be different from that of the presently known chemokine receptors on monocytes. The physiological relevance of the findings is supported by the fact that galectin-3 also selectively recruits monocytes and neutrophils in vivo in a mouse air pouch model.

The finding that galectin-3 is a chemoattractant for macrophages in addition to monocytes is noteworthy, because unlike monocytes, there are few chemokines that have been shown to attract mature macrophages (see Zlotnik et al., *Crit. Rev. Immunol.* 19:1–47 (1999)). The major monocyte chemoattractant MCP-1, for example, is inactive in this respect. Galectin-3 may be a major factor involved in the influx of macrophages to inflammatory sites. Therefore, galectin-3 may have particular therapeutic utility in attracting macrophages to sites where it would be desirable to increase the presence of this cell type.

Galectin-3 -deficient mice develop significantly reduced numbers of peritoneal macrophages compared to wild-type mice when treated with thioglycollate intraperitoneally (Hsu, et al., *Am. J. Pathol.* 156:1073–83 (2000)). This is highly consistent with the findings of the present invention.

Together, these findings suggest that galectin-3 released by the peritoneal cells in thioglycollate-treated mice is responsible, at least in part, for recruiting monocytes and macrophages to the peritoneal cavity. Thus, galectin-3-deficient mice exhibit a lower macrophage response due to the absence of this chemoattractant.

Accordingly, the present invention provides a method for modulating migration of a cell that expresses a galectin-3 receptor comprising contacting the cell with a migration-modulating amount of galectin-3, galectin-3 binding polypeptide, or galectin-3 receptor binding polypeptide. In one embodiment, the invention relates to a method for modulating monocyte, neutrophil or macrophage migration comprising contacting a monocyte, neutrophil or macrophage with a migration-modulating amount of galectin-3, galectin-3 binding polypeptide, or galectin-3 receptor binding polypeptide.

As used herein, "migration modulating-amount" refers to any amount of galectin-3 or galectin-3 binding polypeptide that produces a statistically significant change in the migration of a cell. "Migration" refers to the movement of a cell or group of cells from one location to another. It is intended that migration refer to cell movement resulting from both kinesis (in which the speed or of frequency of cell movement, or cell turning behavior is affected) as well as taxis (in which the direction of cell movement is affected). As demonstrated by the examples described below, cell migration may be modulated according to the present invention both in vitro and in vivo. In vitro migration can be performed, for example, in Boyden chambers. According to one embodiment, migration is modulated in an animal, preferably a mammal, which may be an experimental animal. In one aspect of the invention, the animal is a mouse. In another aspect, the migration may be in a veterinary animal or human, e.g., with a wound, infection, surgical incision, localized or systemic inflammation, tumor or other condition in which it would be desirable to modulate the migration of cells.

Galectin-3 may be produced by any method known in the art. For example, galectin-3 may be purified from cells or tissues normally expressing the polypeptide. Galectin-3 produced by epithelial cells, a major source of this lectin, can contribute to the attraction of monocytes and macrophages during inflammation, and may therefore provide a source of galectin-3 for the methods of the invention. Monocytes and macrophages also produce galectin-3, which may be utilized in the methods of the invention. Any species of animal, including humans, may provide the source material for galectin-3 production, including body fluids such as blood, tissues or cells, including cells expanded using cell culture techniques. The lectin from theses sources may mediate a continued influx of these cell types once the inflammatory process is initiated. Galectin-3 may also be produced by expressing a recombinant galectin-3 polynucleotide in an appropriate host, such as a bacterial, yeast, insect or animal cell. Galectin-3 polynucleotides includes those that are known in the art or functional equivalents or parts of those sequences.

The term "functional" is used herein to refers to any modified version of for example, a nucleotide or polypeptide which retains the basic function of its unmodified form. As an example, it is well-known that certain alterations, mutations or polymorphisms in amino acid or nucleic acid sequences may not affect the polypeptide encoded by that molecule or the function of the polypeptide. It is also possible for deleted versions of a molecule to perform a particular function as well as the original molecule. Even where an alteration does affect whether and to what degree a particular function is performed, such altered molecules are included within the term "functional equivalent" provided that the function of the molecule is not so deleteriously affected as to render the molecule useless for its intended purpose, particularly modulating cell migration.

According to the methods of the invention, migration of cells, including monocytes, neutrophils and macrophages, can be modulated, that is stimulated, inhibited or directed. Recombinant human galectin-3 induces monocyte migration in vitro and it is chemotactic at high concentrations (1.0 µM) but chemokinetic at low concentrations (10–100 nM). As used herein, "chemokinetic" refers to a response by a motile cell to a substance that involves an increase or decrease in speed or frequency of movement or a change in the frequency or magnitude of turning behavior. In contrast, "chemotactic" refers to a response of motile cells in which the direction of movement is affected by the substance. Chemotaxis differs from chemokinesis in that the substance alters probability of motion in one direction only, rather than rate or frequency of random motion in all directions.

The skilled artisan will recognize that the amount of galectin-3, galectin-3 binding polypeptide, or galectin-3 receptor binding polypeptide required to produce a change or modulation in the migration of a cell will depending on the type of cell modulated, the context of that cell (e.g., in vitro versus in vivo; tumor versus wound), and the qualitative change in migration desired. For example, the amount of galetcin-3 required to inhibit cell migration may be different than that required to stimulate cell migration. Similarly, the amount required to reduce generalized cell migration in systemic inflammation may be different than that required to topically enhance cell migration to a localized site of tissue injury.

It has been shown previously that galectin-3 can activate various cell types including induction of superoxide production by monocytes/macrophages (Liu, et al., *Am. J. Pathol.* 147:1016–29 (1995)). Although the precise mechanisms of action still remain to be determined, these activities are probably related to the dimerization or oligomerization of galectin-3 through intermolecular interactions involving the amino-terminal domain (Hsu, et al., *J. Biol. Chem.* 267: 14167–74 (1992)). The lectin thereby becomes bivalent or multivalent functionally and capable of activating cells by effectively crosslinking cell-surface glycoproteins (Barondes, et al., *J. Biol. Chem.* 269:20807–10 (1994); Kasai, et al., *J. Biochem. (Tokyo)* 119:1–8 (1996); Perillo, et al., *J. Mol. Med.* 76:402–12 (1998); Hughes, *Biochem. Soc. Trans.* 25:1194–2298 (1997); Liu, *Immunol. Today* 14:486–90 (1993)). This process may also contribute to the monocyte chemoattractant activity of galectin-3 and this possibility is supported by the finding of the present invention that both the N-terminal and C-terminal domains of galectin-3 are required for this activity. However, an unusual feature of galectin-3's chemoattractant activity is that the response is both qualitatively and quantitatively dependent on the concentration of the lectin. First, galectin-3 is chemokinetic at low concentrations but chemotactic at high concentrations. One possible explanation is that galectin-3 at high concentrations can cause cell aggregation, and, thus, in the checkerboard analysis (described below), when galectin-3 is added to the upper chambers together with the cells, the cells are prevented from migrating towards the lower chambers because they are aggregated. Therefore, it is possible that galectin-3 is actually chemokinetic for monocytes at both high and low concentrations.

However, only monocyte migration induced by high concentrations of galectin-3 is inhibited by PTX. Also, only high concentrations of galectin-3 caused a $Ca^{2+}$ influx in monocytes and this occurred through a PTX-sensitive mechanism(s). The most likely explanation for these findings is that galectin-3 binds to and activates different (or different sets of) cell surface molecules depending on its concentration. At lower concentrations, it preferentially binds to glycoproteins that interact with the lectin relatively strongly, while only after reaching a certain threshold concentration, it begins to recognize other cell surface glycoproteins that interact with the lectin relatively weakly. The latter may include PTX-sensitive G-protein coupled receptor(s). Galectin-3 has been shown to bind to a number of different cell surface glycoproteins on macrophages (Dong and Hughes, *Glycoconjugate J.* 14:267–74 (1997) and, based on a recent study with galectin-1 (Pace, et al., *J. Immunol.* 163:3801–11 (1999), it is likely that the lectin can cause segregation of these different glycoproteins. It is entirely possible that the lectin binds to these different glycoproteins with variable affinity, because they are differentially glycosylated and the lectin exhibits a fine specificity to oligosaccharides (Sparrow, et al., *J. Biol. Chem.* 262: 7383–90 (1987); Leffler and Barondes, *J. Biol. Chem.* 261: 10119–26 (1986); Feizi, *Biochemistry* 33:6342–49 (1994)).

Relatively high concentrations of galectin-3 are needed for the demonstration of optimal experimental chemoattractant activity. The situation is analogous to other activities demonstrated for this lectin previously, such as activation of inflammatory cells (Liu, et al., *Am. J. Pathol.* 147:1016–29 (1995); Frigeri, et al., *Biochemistry* 32:7644–49 (1993); Yamaoka, et al., *J. Immunol.* 154:3479–87 (1995)), and is probably related to the concentrations that are required for the dimerization or oligomerization of the lectin to take place. However, galectin-3 is known to exist at relatively high concentrations in the cytosol of many cell types (e.g., 5 μM in a human colon adenocarcinoma cell line, T84 (Huflejt, et al., *J. Biol. Chem.* 272:14294–303 (1997)). Therefore, a high local concentration of the lectin may be achieved when there is a burst release of the protein from these cells. In fact, galectin-3 has been found to be present in significant amounts in biological fluids. For example, the concentrations of galectin-3 in bronchoalveolar lavage fluid from mice with airway inflammation were found to be over 20 nM. Considering the dilution factor introduced in obtaining the lavage fluid, it is easily conceivable that the initial local concentrations of the lectin are in the micromolar range. On the other hand, the effective concentrations of galectin-3 for attracting alveolar macrophages are much lower (FIG. 10), approaching those typically found for many chemokines. It is possible that the putative receptor for galectin-3 on these cells either exists in higher numbers or interacts with the lectin more strongly. Alternatively, the putative receptor on these cells transmits signals more effectively upon interacting with the lectin.

Galectin-3 probably activates PTX-sensitive G-protein-coupled receptors similar to those recognized by many known chemokines (Baggiolini, *Nature* 392:565–68 (1998); Sallusto, et al., *Immunol. Today* 19:568–74 (1998)). This lectin does not have significant sequence similarity with any of these chemokines, and thus it appears unlikely that it recognizes these receptors through protein-protein interactions, but it could do so via lectin-carbohydrate interactions. Chemokine receptors expressed on monocytes include CCR-1, CCR-2, CCR-5, and CXCR-4 (Baggiolini, *Nature* 392:565–68 (1998); Sozzani, et al, *J. Immunol.* 150:1544–53 (1993)); Bizzari, et al., *Blood* 86:2388–94 (1995); Oberlin, et al, *Nature* 382:833–35 (1996); Sallusto, et al., *Immunol. Today* 19:568–74 (1998)). However, no cross-desensitization has been observed between galectin-3 and any of the monocyte-reactive chemokines that utilize these receptors, including MCP-1 for CCR-2, MIP-1α for CCR-1 and CCR-5, and SDF-1α for CXCR-4. Neither have interactions between galectin-3 and these four chemokine receptors been detected by immunoprecipitation and immunoblotting using specific antibodies. It has been reported that CCR-3 may be also expressed on human monocytes and macrophages (Fantuzzi, et al., *Blood* 94:875–83 (1999)). However, the usage of this receptor was not analyzed because galectin-3 does not attract eosinophils (which are known to express CCR-3) in vitro (not shown) or in vivo (FIG. 11), suggesting no interaction of galectin-3 with this receptor. Therefore, although the precise receptor for galectin-3 remains undetermined, it is not any of the known receptors, such as CCR-1, CCR-2, CCR-3, CCR-5 and CXCR-4.

Other types of chemoattractant receptors, including those for N-formyl-Met-Leu-Phe (fMLP), platelet activating factor (PAF), leukotrienes, and C5a, could mediate the effects of galectin-3. Galectin-3 is also known to recognize CD11b, LAMPs1 and 2, Mac-3, and CD98 on thioglycollate-stimulated mouse peritoneal macrophages (Dong and Hughes, *Glycoconjugate J.* 14:267–74 (1997). Stimulation and/or cross-linking of CD11b and CD98 could enhance adhesion and transendothelial migration of monocytes (Meerschaert and Furie, *J. Immunol.* 154:4099–112 (1995); Fenczik, et al., *Nature* 390:81–85 (1997)).

Figure 7:
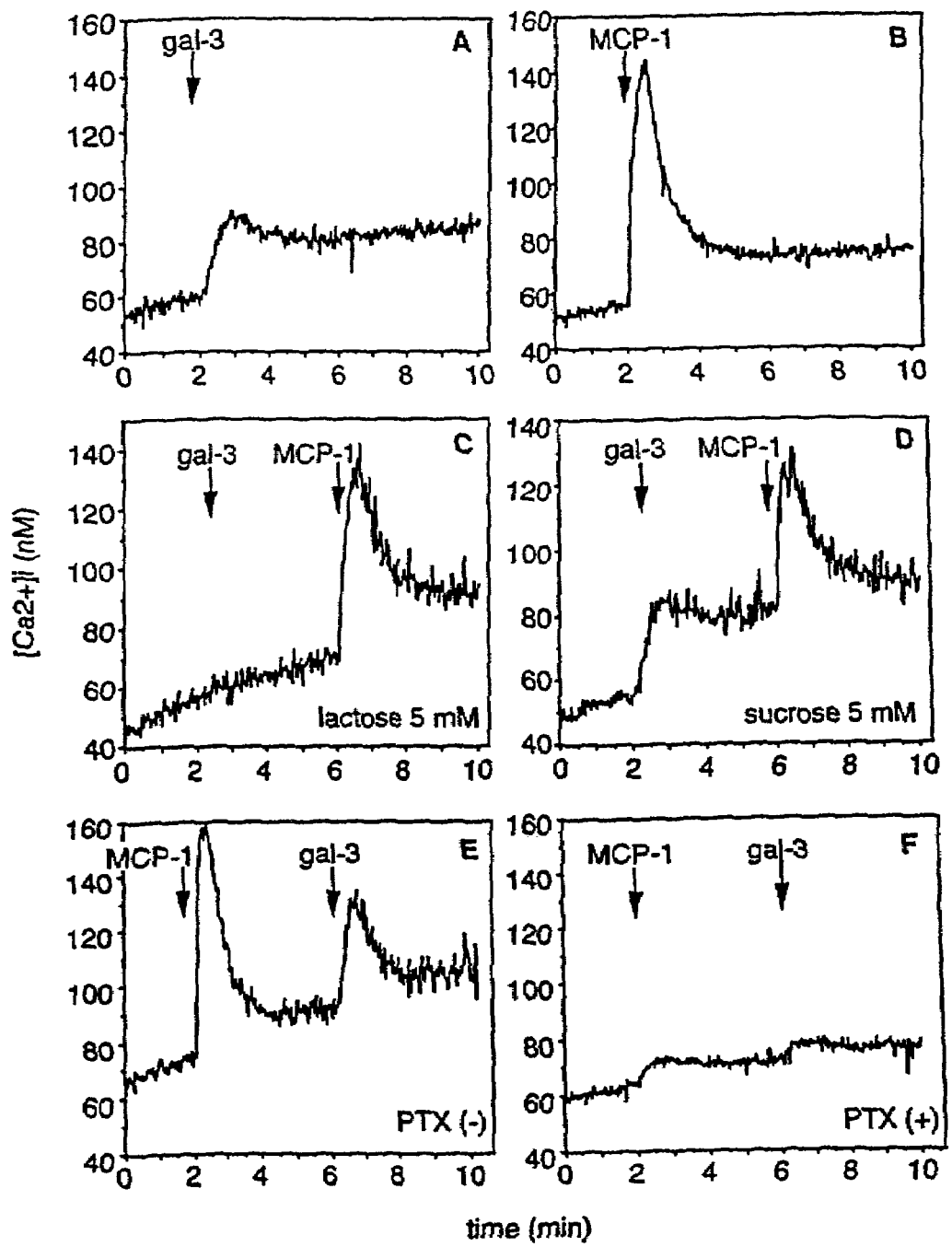
FIGS. 7A–F illustrate the effect of galectin-3 and MCP-1 on $Ca^{2+}$ mobilization in monocytes. Traces represent the average mobilized intracellular concentrations of $Ca^{2+}$ in the examined monocytes. The final concentrations of galectin-3 and MCP-1 in the cell suspensions were 1 μM and 100 ng/ml, respectively. Panels A and B: Effect of galectin-3 (A) and MCP-1 (B) on $Ca^{2+}$ influx in monocytes, respectively. These reagents were added to the cell suspensions at 2 min after the initiation of the measurement. Panels C and D: Effect of two different sugars on galectin-3-induced $Ca^{2+}$ influx in monocytes. After 5 mM lactose (C) or sucrose (D) was mixed with the cell suspension, galectin-3 and MCP-1 were added as the first and the second stimulants at 2 and 6 min after the start of the measurement. Panels E and F: Effect of PTX on galectin-3-induced $Ca^{2+}$ influx in monocytes. Monocytes were incubated in the presence or absence of 1 μg/ml of PTX (together with Indo-1 AM) for 45 min prior to the assay. MCP-1 and galectin-3 were sequentially added to the monocyte suspensions, in the presence of the same concentration of PTX. Each figure shows representative data from 3 individual experiments using different donors.
Figure 11:
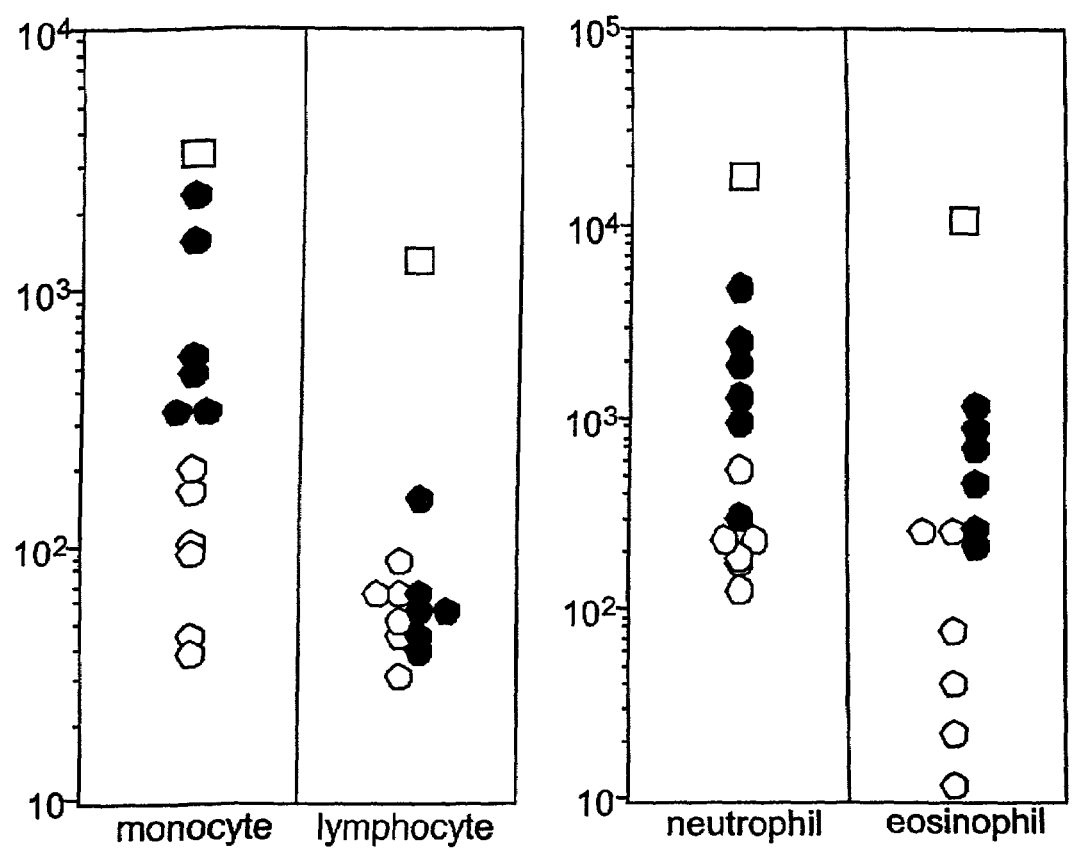
FIG. 11 shows the effect of galectin-3 on monocyte/macrophage recruitment in mouse air pouches. One μM galectin-3 (●) (n=4), vehicle only (○) (n=4), or 100 ng/ml of MCP-1 (□) (n=1) were injected into the pouches as described in Materials and Methods. Each mark represents the cell number from an individual mouse. After a 4 h incubation, the recruited cells were recovered, counted, and analyzed after cytospin preparation and Wright staining.

According to the methods of the invention, the cell type modulated may be any cell type that expresses a galectin-3 receptor and for which galectin-3 has an effect upon cell migration. It is to be noted that while galectin-3 is likely to bind to a number of different cell types through lectin-carbohydrate interactions, its chemoattractant activity is cell-type specific, as it does not induce migration of lymphocytes in vitro, or in vivo as shown in FIG. 11. This selectivity could be explained by the differential expression of the putative galectin-3 receptor on different cell types. For example, galectin-3 is known to cause a $Ca^{2+}$ influx in Jurkat T cells, but the effect was sustained and insensitive to PTX (Dong and Hughes, *FEBS Lett.* 395:165–69 (1996), in contrast to the case in monocytes (FIG. 7). Thus, this lectin can use different receptors on different cell types, resulting in the activation of selected types of cells, or causing a similar effect(s) on different types of cells by alternative pathways. Furthermore, galectin-3 may be a chemoattractant for neutrophils and eosinophils as well. Lower concentrations of this lectin were required for maximum migration of neutrophils compared with monocytes. In addition, galectin-3-induced recruitment of neutrophils in the mouse air pouch experiments (FIG. 11) and . The neutrophil chemoattractant activity of galectin-3 is also consistent with the results obtained from studies of galectin-3-deficient mice by other investigators (Colnut, et al., *Immunol.* 94:290–96 (1998)), who noted that galectin-3 deficiency results in a significantly lower degree of neutrophil response in the peritoneal cavity following thioglycollate stimulation.

Galectin-3 may also play an important role in the function of mast cells. Bone marrow-derived mast cells (BMMC) from wild type [gal-3 (+/+)] and galectin-3 deficient [gal-3 (−/−)] mice show comparable expression of IgE receptor and c-kit. However, upon activation by both FceRI cross-linking and calcium ionophore stimulation, gal-3 (−/−) BMMC secrete a less histamine, b-hexosaminidase and pro-inflammatory cytokine TNF- than gal-3 (+/+) BMMC. Gal-3 (−/−)

BMMC grow poorly in culture as compared to gal-3 (+/+) BMMC, suggesting that galectin-3 may be involved in the regulation of apoptosis of mast cells. When these cells are deprived of growth factors, apoptosis is differentially induced: more apoptosis is observed in 3-week old gal-3 (−/−) BMMC than in gal-3 (+/+) BMMC. However, 4-week old gal-3 (−/−) BMMC are more resistant to apoptosis, suggesting a that there is a defect in signal transduction in gal-3 (−/−) BMMC. Further support for this conclusion is found in the strikingly lower basal level of c-jun-N-terminal kinase (JNK) in cell lysates from gal-3 (−/−) BMMC than in gal-3 (+/+) BMMC (as detected by immunoblotting). In contrast, comparable levels of several other kinases are detectable in the cell lysates from the two genotypes. Further, our results show that JNK is inducible in vitro in both gal-3 (+/+) and gal-3 (−/−) BMMC upon FceRI cross-linking, but immunoprecipitates from gal-3 (−/−) BMMC have significantly reduced ability to phosphorylate the JNK substrate c-jun in an in vitro kinase assay.

In one aspect of the invention, the galectin-3 comprises an N-terminal or C-terminal subsequence of galectin-3. Both the N-terminal and C-terminal domains of galetin-3 appear to be involved in the migration-modulation activity, which can be inhibited by either lactose or the C-terminal domain fragment. Specific monoclonal antibody to galectin-3 was found to inhibit the activity. Thus, the methods of the invention can be practiced using a galectin-3 binding protein, such as a galectin-3 antibody or binding fragment thereof.

As used herein, the term "antibody" refers to intact antibody molecules as well as fragments thereof, such as Fab, F(ab')2, Fv and scFv fragments, which are capable of binding the epitopic determinant. Methods for producing both polyclonal and monoclonal antibodies and monoclonal antibodies are well known in the art (see, for example, Harlow and Lane, *Antibodies: A Laboratory Manual*, Cold Spring Harbor Laboratory (1988)).

Antibodies that bind galectin-3 can be prepared, for example, using intact polypeptides or fragments containing small peptides of interest as the immunizing antigen. The polypeptides or peptides used to immunize an animal can be derived for example, from protein isolated from cells or tissues, by translation of mRNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

Antibodies according to the present invention also include recombinant antibody molecules, or fragments thereof, expressed from cloned antibody-encoding polynucleotides, such as polynucleotides isolated from hybridoma cells or selected from libraries of naturally occurring or synthetic antibody genes (see for example, Gram et al., *Proc. Natl. Acad. Sci. USA* 89:3576–80 (1992)). Humanized antibodies are also contemplated by the present invention. The term "humanized antibody", as used herein, refers to antibody molecules in which amino acids have been replaced in the non-antigen binding regions in order to more closely resemble a human antibody, while still retaining the original binding ability.

The skilled artisan will recognize that galectin-3 receptor binding polypeptides may have the same effect as galectin-3 by acting as agonists of galectin-3 receptors. Polypeptides that bind galectin-3 receptors may also behave as antagonists, thereby competing with galectin-3. Both types of galectin-3 receptor binding polypeptides may be used to modulate migration of a cell and are therefore within the scope of this invention.

The methods of the present invention may be useful in therapeutic applications where it is desirable to increase or decrease the number or rate of migration of cells, particularly migration of cells of the immune system to the site of inflammation, infection or a tumor. "Infection" as used herein, refers to the invasion and multiplication of foreign microorganisms such as bacteria, fungi including yeast, viruses and the like, in body tissues of a host organism, particularly a human. Infections may be unapparent, but frequently are harmful to the normal functioning of the host organism, resulting in local cellular injury due to competitive metabolism, toxins, intracellular replication or antigen-antibody response. The infection may remain localised, subclinical and temporary if the body's defensive mechanisms are effective. A local infection may persist and spread by extension to become an acute, subacute or chronic clinical infection or disease state. A local infection may also become systemic when the microorganisms gain access to the lymphatic or vascular system.

The term "inflammation" as used herein, is a pathologic process of cytologic and chemical reactions that occur in affected blood vessels and adjacent tissues in response to an injury or abnormal stimulation caused by a physical, chemical, or biologic agent. Inflammatory processes include: the local reactions and resulting morphologic changes; the destruction or removal of the injurious material; and the responses that lead to repair and healing. The typical signs of inflammation are redness, heat or warmth, swelling, pain, and occasionally inhibited or lost function. All of the signs may be observed in certain instances, although any particular sign is not necessarily always present. Inflammation often accompanies and is a response to infection or other injury, however, chronic and autoimmue inflammation represent undesirable pathological conditions in which infection is not typically present.

It is envisioned that methods of the present invention may be useful in the treatment of infection and inflammation. For example, galection-3-mediated increases in the migration of cells to the site of an infection or wound may accelerate the eradication of invading microorganisms of infection. Furthermore, galectin-3, galectin-3 binding polypeptides, and galectin-3 receptor binding polypeptides may facilitate localized migration to a desired therapeutic site while limiting migration of destructive cells to surrounding tissue, thereby decreasing tissue damage. In the inflammation phase, inflammatory cells, mostly neutrophils, enter the site of the wound followed by lymphocytes, monocytes, and later macrophages. The neutrophils that are stimulated begin to release proteases and reactive oxygen species (e.g., superoxide) into the surrounding medium with potential adverse effects on both the invading microorganisms and adjacent tissues. For example, the adhesion and spreading of activated neutrophils and monocytes to vascular endothelial cells with the subsequent release of toxio-oxidative metabolites and proteases has been implicated in the organ damage observed in diseases, such as, adult respiratory distress syndrome (ARDS; shock lung syndrome), glomerulonephritis, and inflammatory injury occurring after reperfusion of ischemic tissue such as to the heart, bowel, and central nervous system. (see, e.g., Harlan, *Blood*, 65: 513–525 (1985)).

Accordingly, methods for increasing migration of monocytes, neutrophils or macrophages to an inflammatory or infection site are provided comprising contacting the inflammatory or infection site, respectively with a migration-increasing amount of galectin-3, galectin-3 binding polypeptide or galectin-3 receptor binding polypeptide.

Methods are also provided for increasing migration of monocytes, neutrophils or macrophages to a tumor comprising contacting the tumor with a migration-increasing amount of galectin-3, galectin-3 binding polypeptide, or galectin-3 receptor binding polypeptide. "Tumor," according to the present invention is any abnormal mass of tissue that results from excessive cell division that is uncontrolled and progressive. Tumors are also referred to as neoplasms. Tumors perform no useful body function. They may be either benign (not cancerous) or malignant and include localized as well as metastatic growths which may spread to locations distant to the site of the original tumor cell. It has been postulated that the basis for neoplastic development lies in the ability of an initial tumor cell to evade immune surveillance mechanism. Methods of enhancing immune surveillance of tumor cells, such as increasing monocyte, neutrophil or macrophage migration to a tumor, either alone or in combination with other therapy, may therefore prove useful in treating neoplastic diseases such as cancer.

The present invention also provides a method for indentifying an agent that modulates galectin-3 mediated cell migration comprising: contacting galectin-3 with a test agent; and detecting galectin-3 mediated cell migration, wherein an alteration of galectin-3 meditated cell migration in the presence of the test agent identifies an agent that modulates galectin-3 mediated cell migration. Agents according to the method may either increase or decrease galectin-3 mediated cell migration. In one embodiment, the agent is a small molecule, which may be naturally occurring or synthetic. In other embodiments, the agent may for example, be a co-factor, vitamin, hormone, enzyme, accelerant, stimulant, agonist, mimetic, antagonist, inhibitor, analog, ligand, or derivative. Also included are naturally occurring and synthetic biologicals, including proteins, peptides, polypeptides, lipids, carbohydrates, polysaccharides and sugars.

According to the method, galectin-3 may be contacted in vitro, such as in a test tube or other suitable vessel prior to or concurrent with detecting galectin-3 mediated migration. In one galectin-3 is contacted in vitro utilizing a micro Boyden chamber as described below. Contact may also occur intracellularly. Non-limiting examples of contacting galectin-3 intracellularly includes contacting intracellular or newly-synthesized forms of galectin-3 with agents capable of entering the cell, such as by diffusion or by active transport. Agents, including genes encoding biologicals such as polypeptides, may also be physically introduced into cells by such techniques as microinjection, electroporation, or transfection. Galectin-3 may also be contacted in vivo, such as by administering a systemic or local dose of an agent to an experimental animal. The agent may be administered by any route that places the agent in contact with galectin-3 in the animal. The dose may, for example, be administered subcutaneously (as described in Example 8 below) or intraperitoneally (as described below in Example 9).

The agent may interact directly or indirectly with galectin-3 to increase or decrease the effectiveness of galectin-3 in mediating cell migration. Also contemplated by the invention are agents that interact with galectin-3 receptors or other cellular structures. Such agents may, for example, block galectin-3 binding, thereby reducing cell migration mediated by either endogenous or exogenous galectin-3 in an organism. Conversely, agents that interact with galectin-3 receptors may act as agonists, thereby increasing galectin-3 mediated cell migration. Agents that act upon other components in galectin-3-mediated signal transduction pathways are non-limiting examples of additional agents contemplated by the invention.

Also provided by the present invention is an antibody that specifically binds galectin-3. One embodiment of the invention provides compositions containing migration-modulating amount galectin-3 antibodies and a pharmaceutically acceptable carrier, excipient or diluent.

Compositions comprising galectin-3 or a functional subsequence thereof and a pharmaceutically acceptable carrier, excipient or diluent are also included in the invention. "Functional subsequence" refers to any fragment or portion of galectin-3 possessing the desired experimental, clinical or therapeutic property of the intact galectin-3 molecule. Subsequences may be prepared by any means known in the art, such as by proteolytic digestion of intact, full-length galectin-3, by cloning and expressing fragments of a galectin-3 gene, or by synthesis of peptides by known chemical techniques.

In one aspect of this embodiment, compositions containing galectin-3 also contain a drug. The drug may include any compound, composition, biological or the like that potentiates, stabilizes or synergizes with galectin-3. Also included are drugs that may be beneficially or conveniently provided at the same time as galectin-3, such as drugs used to treat the same, a concurrent or a related symptom, condition or disease. In preferred embodiments, the drug may include without limitation anti-tumor, antiviral, antibacterial, anti-mycobacterial, anti-fungal, anti-cell proliferative or apoptotic agent. Drugs that are included in the compositions of the invention are well known in the art (see e.g., *Goodman & Gilman's The Pharmacological Basis of Therapeutics*, $9^{th}$ Ed. (Hardman, et al., eds) McGraw-Hill (1996) herein incorporated by reference).

Compositions of the present invention may be administered according to dosage regimens established in the art whenever specific pharmacological modification of galectin-3-mediated cell migration is desirable.

The present invention also provides pharmaceutical compositions comprising one or more compounds of the invention together with a pharmaceutically acceptable diluent, excipient, or carrier. Preferably such compositions are in unit dosage forms such as tablets, pills, capsules (including sustained-release or delayed-release formulations), powders, granules, elixirs, tinctures, syrups and emulsions, sterile parenteral solutions or suspensions, aerosol or liquid sprays, drops, ampoules, auto-injector devices or suppositories; for oral, parenteral (e.g. intravenous, intramuscular or subcutaneous), intranasal, sublingual or rectal administration, or for administration by inhalation or insufflation, and may be formulated in an appropriate manner and in accordance with accepted practices such as those disclosed in *Remington's Pharmaceutical Sciences*, (Gennaro, ed., Mack Publishing Co., Easton Pa., 1990, herein incorporated by reference). Alternatively, the compositions may be in sustained-release form suitable for once-weekly or once-monthly administration; for example, an insoluble salt of the active compound, such as the decanoate salt, may be adapted to provide a depot preparation for intramuscular injection. The present invention also contemplates providing suitable topical formulations for administration to, e.g. eye, skin or mucosa.

For instance, for oral administration in the form of a tablet or capsule, the active pharmacological drug component can be combined with an oral, non-toxic pharmaceutically acceptable inert carrier such as ethanol, glycerol, water and the like. Moreover, when desired or necessary, suitable binders, lubricants, disintegrating agents, flavoring agents and coloring agents can also be incorporated into the mixture. Suitable binders include, without limitation, starch, gelatin, natural sugars such as glucose, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For preparing solid compositions such as tablets, the active ingredient is mixed with a suitable pharmaceutical excipient, e.g. such as the ones described above, and other pharmaceutical diluents, e.g. water, to form a solid preformulation composition containing a homogeneous mixture of a compound of the present invention, or a pharmaceutically acceptable salt thereof. By the term "homogeneous" is meant that the active ingredient is dispersed evenly throughout the composition so that the composition may be readily subdivided into equally effective unit dosage forms such as tablets, pills and capsules. The solid preformulation composition may then be subdivided into unit dosage forms of the type described above containing from 0.001 to about 500 mg of the active ingredient of the present invention. The tablets or pills of the present composition may be coated or otherwise compounded to provide a dosage form affording the advantage of prolonged action. For example, the tablet or pill can comprise an inner core containing the active compound and an outer layer as a coating surrounding the core. The outer coating may be an enteric layer that serves to resist disintegration in the stomach and permits the inner core to pass intact into the duodenum or to be delayed in release. A variety of materials can be used for such enteric layers or coatings, such materials including a number of polymeric acids and mixtures of polymeric acids with conventional materials such as shellac, cetyl alcohol and cellulose acetate.

The liquid forms in which the present compositions may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical carriers. Suitable dispersing or suspending agents for aqueous suspensions include synthetic and natural gums such as tragacanth, acacia, alginate, dextran, sodium carboxymethylcellulose, gelatin, methylcellulose or polyvinylpyrrolidone. Other dispersing agents that may be employed include glycerin and the like. For parenteral administration, sterile suspensions and solutions are desired. Isotonic preparations, which generally contain suitable preservatives, are employed when intravenous administration is desired. The compositions can also be formulated as an ophthalmic solution or suspension formation, i.e., eye drops or ointment, for ocular administration Consequently, the present invention also relates to a method of alleviating or treating a disease, symptom or condition in an animal in which galectin-3-mediated modulation of cell migration, in particular modulation of monocytes, macrophages, and/or neutrophils, has a beneficial effect, by administering a therapeutically effective amount of a galectin-3, a functional subsequence thereof, a galectin-3 binding polypeptide or a galectin-3 receptor binding polypeptide, such as an antibody or other compositions of the present invention to a subject in need of such treatment. Such diseases or conditions may, for instance arise from inappropriate, undesirable or inadequate migration of monocytes, macrophages, and/or neutrophils, such as encountered in inflammation, infection, and neoplasia.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes palliation or alleviation of any of the symptoms of the disease being treated. Particularly, therapeutically effective amounts of the compositions of the present invention may be useful for treating the symptoms of inflammation, infection and neoplasia.

Advantageously, compositions of the present invention may be administered in a single daily dose, or the total daily dosage may be administered in divided doses two, three, four or more times daily. Furthermore, compounds for the present invention may be administered in intranasal form via topical use of suitable intranasal vehicles, or via transdermal routes, using those forms of transdermal skin patches well known to persons skilled in the art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound employed. A physician or veterinarian of ordinary skill can readily determine and prescribe the effective amount of the drug required to prevent, counter the progress of, or arrest or alleviate the symptoms of the disease or disorder that is being treated.

The daily dosage of the products may be varied over a wide range, such as from 0.001 to 100 mg per adult human per day. For oral administration, the compositions are preferably provided in the form of tablets containing 0.001, 0.01, 0.05, 0.1, 0.5, 1.0, 2.5, 5.0, 10.0, 15.0, 25.0, 50.0, 100.0, 250.0, or 500.0 mg of the active ingredient for the symptomatic adjustment of the dosage to the patient to be treated. A unit dose typically contains from about 0.001 mg to about 500 mg of the active ingredient, preferably from about 0.1 mg to about 100 mg of active ingredient, more preferably from about 1.0 mg to about 10 mg of active ingredient. An effective amount of the drug is ordinarily supplied at a dosage level of from about 0.0001 mg/kg to about 25 mg/kg of body weight per day. Preferably, the range is from about 0.001 to 10 mg/kg of body weight per day, and especially from about 0.001 mg/kg to 1 mg/kg of body weight per day. The compounds may be administered on a regimen of, for example, 1 to 4 or more times per day.

Compositions according to the present invention may be used alone at appropriate dosages defined by routine testing in order to obtain optimal pharmacological effect on cell migration, in particular monocyte, macrophage, and/or neutrophil migration, while minimizing any potential toxic or otherwise unwanted effects. In addition, co-administration or sequential administration of other agents or drugs, which improve the effect of the compositions of the invention may, in some cases, be desirable. For example, it may be desirable to administer galectin-3 or a functional subsequence thereof together with anti-tumor, antiviral, antibacterial, anti-mycobacterial, anti-fungal, anti-cell proliferative or apoptotic agent.

According to the present invention, compositions comprising galectin-3 or a functional subsequence thereof and an article of manufacture are also included. In one embodiment, the article of manufacture comprises a dressing. Preferably, the dressing is a bandage, suture, sponge, or a surgical dressing. Bandages, sutures, sponges or surgical dressings may be made of any suitable material known in the art, such as cotton gauze, adhesive tapes (including paper), latex, Dacron, Gortex, nylon, Prolene, Vicryl and gut. In one aspect, the article of manufacture facilitates delivery of the galectin-3, subsequence, or another composition, such as a drug. In another aspect, the article of manufacture provides a related function, such as promoting wound healing, maintaining sterility of a surgical site or facilitating drainage.

The compositions of the invention may advantageously be administered in a depot or sustained release form. Alternatively, administration may be by continuous or intermittent infusion, injection, insufflation or infiltration. The invention therefore includes a microfabricated device containing galectin-3 or a functional subsequence thereof in a pharmaceutically acceptable carrier, the device capable of controlled delivery of the galectin-3 or the functional subsequence. "Microfabricated device" refers to a structure having chambers and at least way-one flow, generally accommodating small volumes; for example, chambers generally accommodate volumes that range from about 0.01 µl to about 10 ml. In one embodiment, the device includes an internal or external pump. In a preferred embodiment, the device can be implanted in the body of a subject. In various aspects the device may be implanted at the site of infection, in close proximity to or within a solid tumor or at the site of a lesion.

The following examples further illustrate the present invention, but should not be construed as in any way limiting its scope.

EXAMPLES

A. Materials

Recombinant human galectin-3 (Hsu, et al., *J. Biol. Chem.* 267:14167–74 (1992)) the C-terminal domain fragment of galectin-3 (galectin-3C) (Yang et al., *Proc. Natl. Acad. Sci. USA* 93:6736–42 (1996)), a mouse monoclonal antibody against galectin-3 (B2C10) (Liu, et al., *Biochemistry* 35:60773–79 (1996)), and mouse monoclonal anti-DNP IgG1 (Liu, et al., *J. Immunol.* 124:2728–31 (1980)) were prepared as described previously. Recombinant MCP-1, MIP-1a, and SDF-1a were obtained from Pepro Tech Ltd. (Rocky Hill, N.J.). Indo-1 AM was from Molecular Probes (Eugene, Oreg.). Hank's Balanced Salt Solution (HBSS) and RPMI 1640 were purchased from Gibco BRL (Grand Island, N.Y.). Ficoll Paque and Percoll solution were obtained from Amersham Pharmacia Biotech AB (Uppsala, Sweden). Unless otherwise stated, all other reagents were purchased from Sigma Chemical Co. (St. Louis, Mo.).

B. Preparation of Human Monocytes

Human monocytes were purified from venous blood of normal volunteers essentially as described previously (Nakagawara, et al., *J. Clin. Invest.* 68:1243–53 (1981)). In brief, after erythrocytes were sedimented by addition of 6% dextran saline solution (1 part to 5 parts heparinized blood), the leukocytes were collected, washed twice, and resuspended in $Ca^{2+}$ and $Mg^{2+}$-free HBSS containing 5% autologous serum. Mononuclear cells were acquired by centrifugation of the leukocyte suspension on Ficoll Paque at 1,500 rpm for 15 min. The cells were resuspended in RPMI 1640 containing 10% autologous serum and allowed to adhere to sterile tissue culture plates for 30 min in a humidified incubator at 5% $CO_2$ and 37° C. After incubation, non-adherent cells were removed by washing the plates three times with PBS at 37° C. Greater than 98% of the adherent cells showed the characteristic appearance of monocytes when examined by light microscopy following Wright staining or neutral red staining. To detach and harvest the adhered monocytes, 1 mM EDTA-PBS containing 5% serum was added and the plates were incubated on ice for 30 min. The monocytes were washed twice with HBSS and resuspended in RPMI 1640 with 0.1% autologous serum for the migration assay. The viability of monocytes was determined by trypan blue exclusion and was more than 98%. In some experiments, monocytes were purified according to another method using a Percoll discontinuous gradient described previously (Chuluyan & Issekutz, *J. Clin. Invest.* 92:2768–77 (1993)). No difference was noted in the purity and viability of the cells prepared by these two different methods.

C. Preparation of Human Cultured Peripheral Blood Macrophages and Alveolar Macrophages Human macrophages were obtained by culturing peripheral blood monocytes in vitro for 7 days as previously described (Fantuzzi, et al., *Blood* 94:875–83 (1999)). Human alveolar macrophages were obtained from bronchoalveolar lavage (BAL) fluid according to a previously described protocol (Sugimoto et al, *Am. Rev. Respir. Dis.* 139:1329–35 (1989)). The purity of the macrophages was over 90% and the viability was over 99%.

D. Migration Assay in Vitro

Monocyte migration was examined by using 96-well micro Boyden chambers with 5 µm-pore size filters (Neuro Probe, Inc., Gaithersburg, Md.) as described previously (Falk, et al., *J. Immunol. Meth.* 33:239–47 (1980)), Chertov, et al, *J. Biol. Chem.* 271:2935–40 (1996)). Briefly, after the indicated concentrations of galectin-3 in RPMI 1640 were applied to the lower chambers, purified monocyte suspensions ($2.5-5.0 \times 10^4$/well) were applied to the upper chambers. After incubation of the chambers for 1 h in a humidified incubator at 5% $CO_2$ and 37° C., the filters were washed once with PBS and processed with Wright stain. The number of monocytes on the bottom side of the filters was counted in 5 to 10 high-power fields. Monocyte migration was calculated from the average numbers of the counted cells and expressed as % of input cells in a well.

In assays using inhibitory reagents, the purified monocytes were pretreated with or without the indicated concentrations of B2C10 (Liu, et al., *Biochemistry* 35:60773–79 (1996)) or anti-DNP IgG1 (Liu, et al, *J. Immunol.* 124: 2728–31 (1980)) as an isotype-matched control mAb, galectin-3C, or PTX at 37° C. for 30 min. Then the cells were applied to the upper chambers in the presence of these inhibitors at the same concentrations used in the pretreatment. In the assays using lactose and sucrose, the sugars were added to the lower chambers at the initiation of the migration assay.

E. Migration Assay in vivo

The mouse air pouch experiments were performed according to a method described previously (Perretti, et al, *J. Immunol.* 151:4306–14 (1993)). Briefly, an air pouch was induced on the back of Balb/c mice by injecting 3 ml of air intradermally 2, 4, and 6 days before the experiments. Then, 1 ml of 0.9% sodium chloride (USP grade saline, Baxter Healthcare Corporation, Deerfield, Ill.) containing 1 µM galectin-3 was injected into the pouch. As positive and negative controls, 100 ng/ml of recombinant MCP-1 and diluent only, respectively, were injected. Four h afterwards, recruited cells were recovered by gently lavaging the pouch with 1 ml of PBS containing 1 mM EDTA. Cell number was determined and the distribution of leukocyte types was analyzed after cytospin preparation and Wright staining.

F. Measurement of $Ca^{2+}$ Influx in Monocytes

Intracellular concentrations of $Ca^{2+}$ were measured by using Indo-1 AM according to a previously described method (Lopez, et al., *Cytometry* 10: 165–73 (1989)). Purified monocytes were resuspended in HBSS containing 1 mM $Ca^{2+}$, 1 mM $Mg^{2+}$, and 5% autologous serum, and incubated with 10 mM Indo-1 AM for 45 min at 37° C. The cells were washed once, resuspended in the same buffer, and stimuli and inhibitors were added at the time points specified in the Figure Legends. Intracellular $Ca^{2+}$ concentration was measured by monitoring light emission at 405 and 485 nm to an excitation wavelength of 355 nm, using an AMINCO-Bowman series 2 luminescence spectrometer (Rochester, N.Y.).

G. Data Analysis

Data are summarized as the mean±Standard Deviation (SD). The statistical examination of the results was performed by the variance analysis using Fisher's protected least significant difference test for multiple comparisons. The analysis of the results from the mouse air pouch experiments was conducted with the Mann-Whitney test. p values of <0.05 were considered significant.

Example 1

Galectin-3 Induces Monocyte Migration in vitro

Using a micro Boyden chamber assay, human recombinant galectin-3 induced monocyte migration in a dose-dependent manner. Galectin-3 significantly increased monocyte migration at concentrations greater than 100 nM compared with diluent (control, 3.54±2.2% vs. 100 nM, 6.25±1.3%; 300 nM, 9.8±0.33%; 1 µM, 12.4±1.2%; p<0.05; n=4 experiments) (FIG. 1). While the difference in the effect between lower concentrations of galectin and control was not statistically significant in these initial experiments, in many subsequent ones, 10 nM galectin-3 also significantly increased monocyte migration (control, 4.26±1.3% vs. 10 nM, 7.01±2.1%; p<0.001; n=21). The effect of 1 µM galectin-3 on monocyte migration was comparable to that of human recombinant MCP-1, a strong chemoattractant for monocytes (Zachariae, et al., *J. Exp. Med.* 171:2177–82 (1990)), at 100 ng/ml (11.6 nM) (FIG. 1), which was determined in dose-response experiments to be the concentration that induced maximum monocyte migration in this assay.

Figure 2:
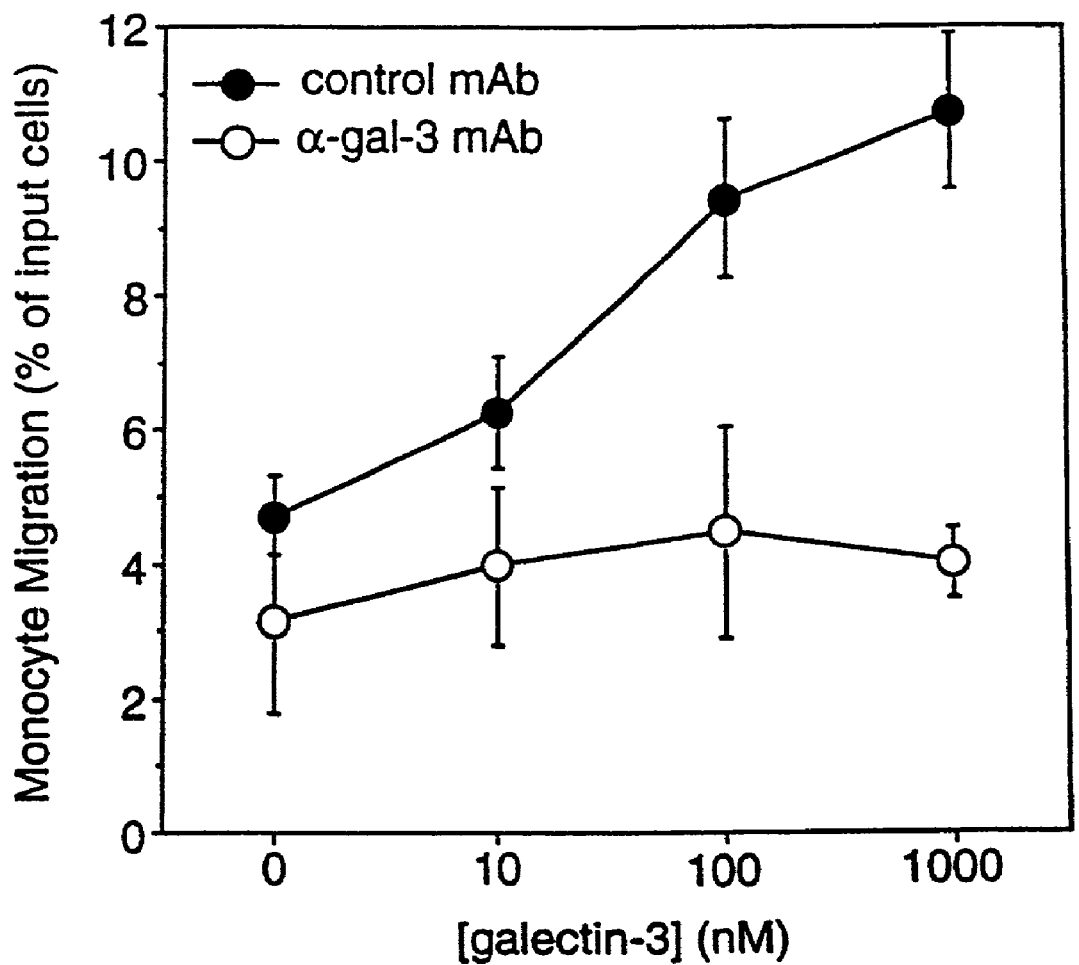
FIG. 2 illustrates the effect of anti-galectin-3 mAb on monocyte migration. After treatment with control (●) or anti-galectin-3 (○) mAb, purified monocytes were added to the upper chambers and the migration assay was performed as described in Materials and Methods. Data are the mean±SD of 3 individual experiments.

To rule out the possibility that the above results were due to contaminating bioactive substances such as heat-stable endotoxins in the recombinant galectin-3 preparations, experiments were conducted using galectin-3 samples pretreated at 100° C. for 5 min, which is known to inactivate this lectin (Yamaoka, et al., *J. Immunol.* 154:3479–87 (1995)). These samples did not induce monocyte migration at any of the concentrations used (10 nM–1 µM) (data not shown). Furthermore, the effect of an anti-galectin-3 mAb B2C10, which has been shown to block the binding of galectin-3 to IgE and neutrophil cell surfaces (Liu, et al., *Biochemistry* 35:60773–79 (1996)), on monocyte migration was studied. 10 µg/ml of B2C10, but not an isotype-matched control mAb, completely inhibited monocyte migration induced by galectin-3 at all concentrations examined (p<0.05, n=3) (FIG. 2). B2C10 did not affect MCP-1-induced monocyte migration significantly. These results indicate that exogenous galectin-3 induces migration of human monocytes in vitro.

Example 2

Figure 3:
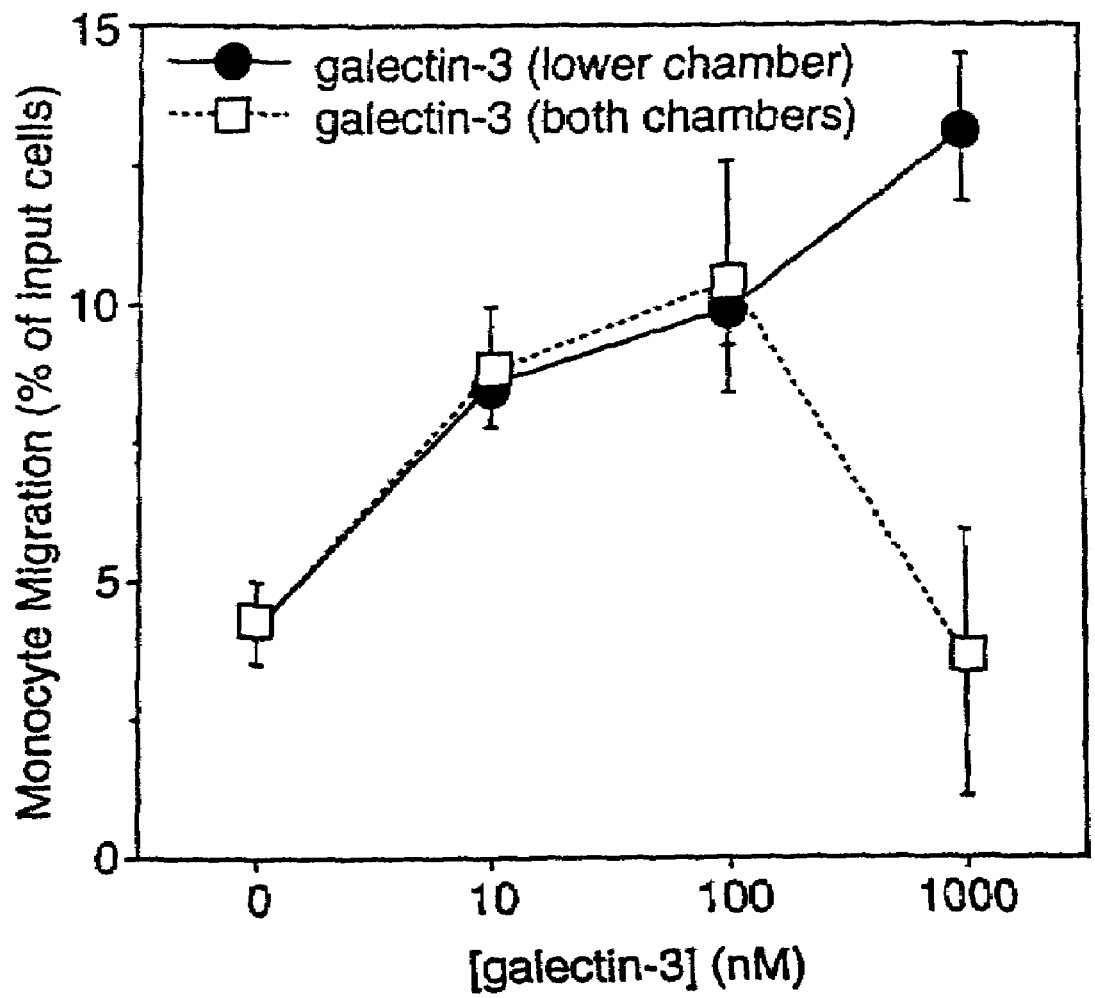
FIG. 3 is a line graph depicting chemotaxis versus chemokinesis in galectin-3-activated monocytes. The data from the checkerboard experiment in Table 1 below has been represented graphically in this figure. Closed circles (●) represent the monocyte migration when galectin-3 was added only to the lower chambers. Open squares (□) show monocyte migration when equal concentrations of galectin-3 were added to both chambers.

Galectin-3 is Chemotactic at High Concentrations and Chemokinetic at Low Concentrations for Monocytes A checkerboard analysis was performed to assess whether galectin-3 is chemotactic or chemokinetic for monocytes. Various concentrations of galectin-3 were applied to the upper and/or lower chambers of a Boyden chamber, and monocyte migration was examined. As shown in Table 1 and FIG. 3, when 10 or 100 nM galectin-3 was used, no significant difference in monocyte migration was observed regardless of whether the protein was added to the lower chambers or to both chambers. In contrast, when 1 µM galectin-3 was added to both chambers, no significant increase in monocyte migration over the background was observed. These results indicate that the effect of galectin-3 in vitro is chemokinetic at low concentrations (10 and 100 nM), but chemotactic at high concentrations (1 µM).

TABLE 1

Checkerboard analysis of the effect of galectin-3 on the attraction of human peripheral blood monocytes in vitro. Various concentrations of galectin-3 were applied to the lower chambers and purified monocytes mixed with various concentrations of galectin-3 were applied to the upper chambers, as described in Materials and Methods. Monocyte migration is expressed as % migrated cells of the total cells. Data are the mean ± SD of 4 individual experiments.

| Below | Above | | | |
|---|---|---|---|---|
|  | 0 | 10 | 100 | 1000 (nM) |
| 0 | 4.23 ± 0.75 | 7.55 ± 0.79 | 10.7 ± 0.86 | 3.30 ± 2.82 |
| 10 | 8.66 ± 0.22 | 8.88 ± 1.09 | 11.4 ± 2.11 | 3.25 ± 3.11 |
| 100 | 9.96 ± 0.72 | 9.23 ± 2.23 | 10.5 ± 2.10 | 4.55 ± 3.69 |
| 1000 | 13.1 ± 1.33 | 11.5 ± 3.49 | 12.5 ± 2.87 | 3.50 ± 2.41 |

Example 3

Figure 4:
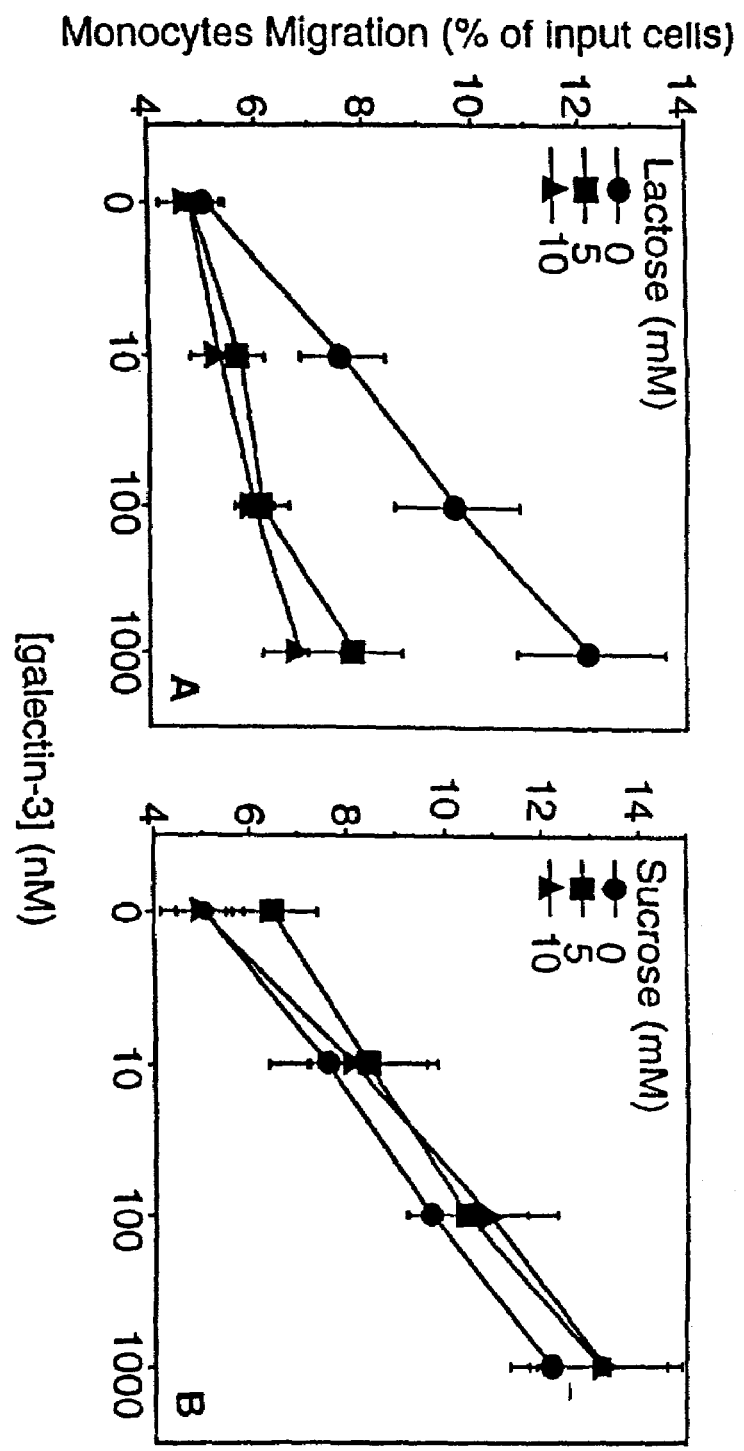
FIG. 4 shows the effect of sugars on galectin-3-induced monocyte migration. Various concentrations of galectin-3 were mixed with 0 mM (●), 5 mM (■), or 10 mM (▲) lactose (panel A) or sucrose (panel B) and placed in the lower chambers. Purified monocytes were added to the upper chambers and a standard migration assay was then performed. Data are the mean±SD of 4 individual experiments.
Figure 5:
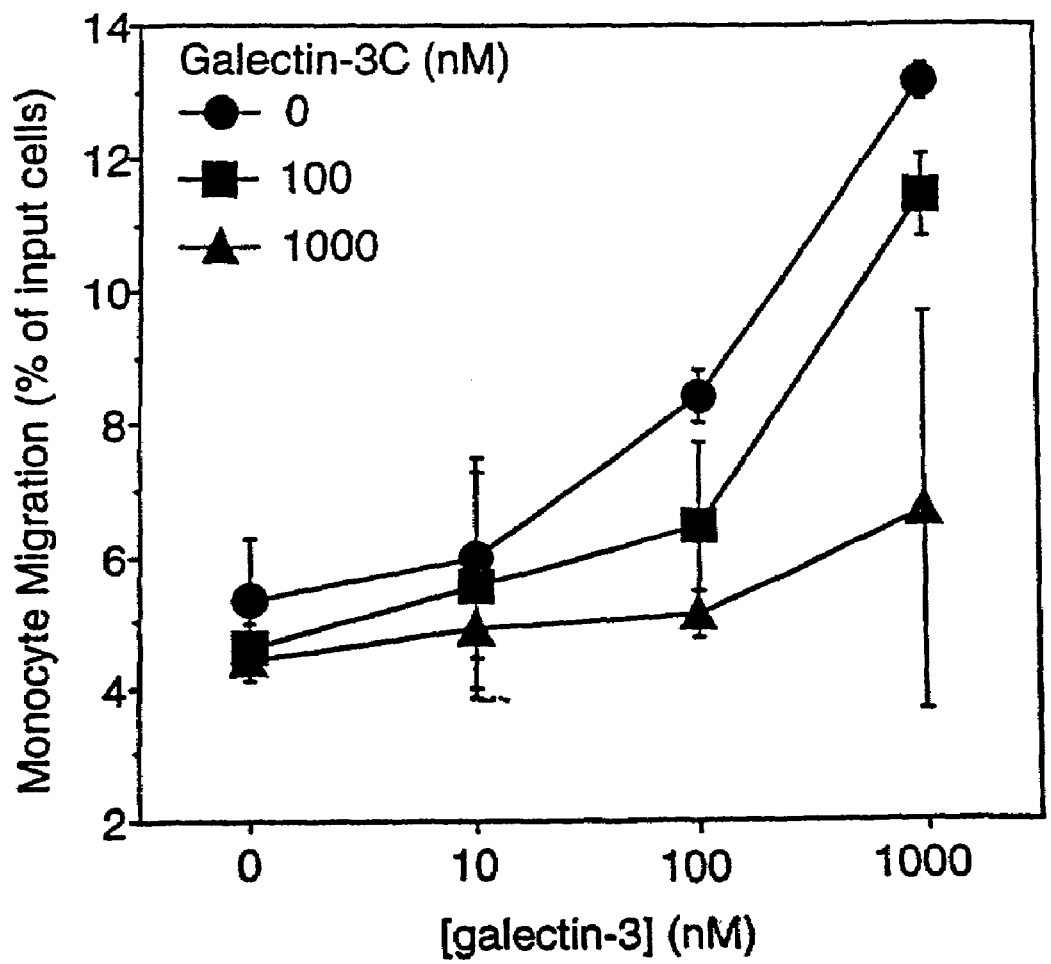
FIG. 5 is a line graph of the effect of a C-terminal domain fragment of galectin-3 (galectin-3C) on galectin-3-induced monocyte migration. After monocytes were incubated with the indicated concentrations of galectin-3C, the cells were added to the upper chambers and a standard migration assay was performed. Data are the mean±SD of 4 individual experiments.

Necessity of N- and C-Terminal Domains of Galetcin-3 for Monocyte Chemoattractant Activity Galectin-3 is composed of a C-terminal lectin domain and an N-terminal non-lectin part. To determine whether the chemoattractant activity of galectin-3 is dependent on its lectin properties, the effect of saccharides on its induction of monocyte migration was tested. As shown in FIG. 4A, 5 mM lactose significantly decreased monocyte migration induced by 10 nM, 100 nM, and 1 µM galectin-3 by 63.8%, 71.5%, and 57.6%, respectively (p<0.05, n=3). Similarly, 10 mM lactose also significantly inhibited the migration by 78%, 74.1%, and 71.1%, respectively (p<0.05, n=3). These concentrations of lactose did not affect the monocyte migration induced by MCP-1. As a negative control, the effect of sucrose, which dose not bind to galectin-3, was also tested. As seen in FIG. 4B, sucrose had no significant effect on monocyte migration. These results indicate that the C-terminal lectin domain of galectin-3 is involved in the induction of monocyte migration.

The effect of a recombinant C-terminal domain fragment of galectin-3 (galectin-3C) on monocyte migration was also examined. Monocytes were preincubated with various amounts of galectin-3C for 30 min at 37° C., the mixture was then applied to the upper chambers, and a standard migration assay was performed. As shown in FIG. 5, 1 μM galectin-3C alone did not have any chemokinetic effect on monocytes, but it significantly inhibited cell migration induced by 100 nM and 1 μM galectin-3 by 77.4% and 45.0%, respectively ($p<0.05$, n=3). Galectin-3C pretreated at 100° C. showed no effect on galectin-3-induced monocyte. No influence on monocyte migration was observed with 100 μM galectin-3C (FIG. 5). These results further confirm the involvement of the lectin domain in the chemoattractant activity and also suggest that the N-terminal domain is also necessary for this activity.

Example 4

Figure 6:
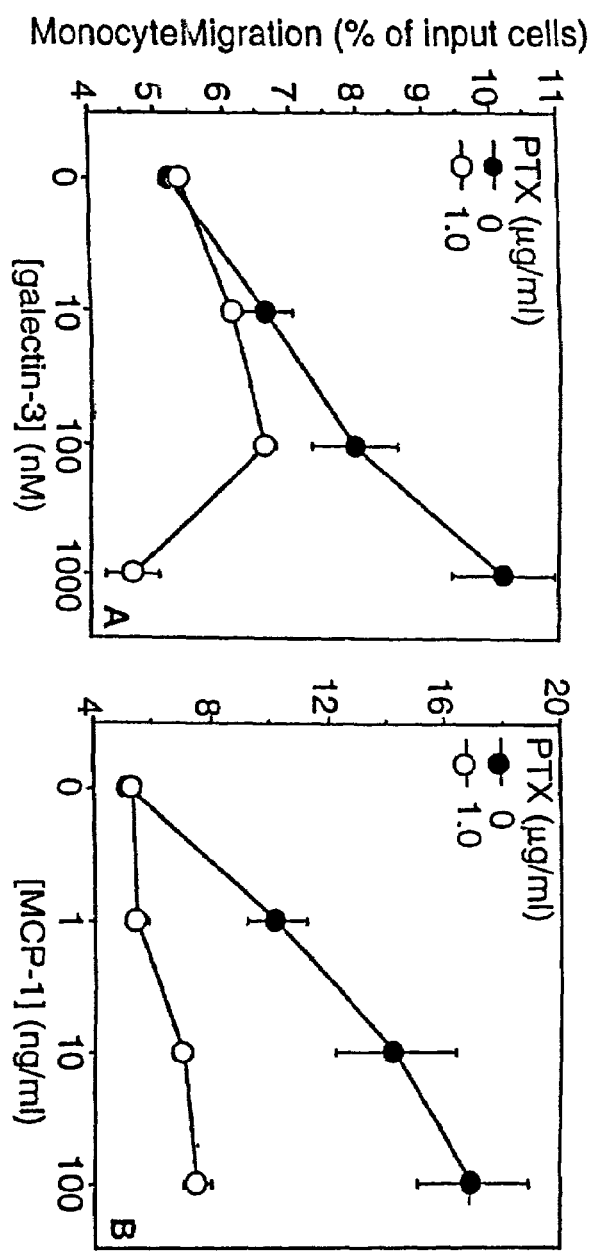
FIGS. 6A and B are a pair of graphs comparing the effect of PTX on monocyte migration. After monocytes were treated with PTX, the cells were added to the upper chambers and the migration towards galectin-3 (panel A) or MCP-1 (panel B) was performed as described in Materials and Methods. Data are the mean±SD of 4 individual experiments.

Galectin-3 Induction of Monocyte Migration by PTX-Sensitive and -Insensitive Pathways The possibility that G-proteins might be involved in galectin-3-induced monocyte migration was tested using the inhibitor pertussis toxin (PTX), because it is well known that many chemoattractants, including all chemokines, utilize G-protein-coupled receptors to transduce signals into the cell (Baggiolini, Nature 392:565–68 (1998)). Preliminarily, it was confirmed that 1 μg/ml of PTX did not decrease the viability of monocytes (data not shown). PTX decreased monocyte migration induced by 1 μM galectin-3 by 91.2% ($p<0.01$, n=5) (FIG. 6A). However, PTX did not significantly inhibit monocyte migration induced by 10 or 100 nM galectin-3 ($p=0.8501$ and 0.3093, respectively; n=5). In contrast, 1 μg/ml of PTX significantly inhibited monocyte migration induced by MCP-1 at all concentrations examined (FIG. 6B). These results indicate that a PTX-sensitive G-protein coupled receptor(s) is(are) involved in monocyte migration induced by high concentrations of galectin-3, but that a PTX-insensitive pathway(s) could be used in attracting monocytes by low concentrations of galectin-3.

Example 5

Galectin-3 Induced Increases in Intracellular Calcium Concentration by a PTX-Sensitive Pathway(s)

Galectin-3 can dimerize and crosslink cell surface receptors, suggesting that galectin-3 is chemotactic because it is able to activate chemokine receptors. To further analyze galectin-3-mediated signaling, the ability of this lectin to induce a $Ca^{2+}$ influx in monocytes, because many chemoattractants are known to cause a $Ca^{2+}$ influx. 1 μM galectin-3, but not lower concentrations, induced a $Ca^{2+}$ influx in human monocytes similar to MCP-1 (FIG. 7A, B), although the extent of the $Ca^{2+}$ influx caused by the lectin was lower than that by the chemokine in all three separate experiments. Heat-inactivated galectin-3 did not produce any response (data not shown). The specificity of this activity was also demonstrated by the complete inhibition of galectin-3- but not MCP-1-induced $Ca^{2+}$ influx by 5 mM lactose but not sucrose (FIG. 7C, D). Furthermore, both the galectin-3- and MCP-1-induced $Ca^{2+}$ influx was blocked by PTX (FIG. 7E, F). These results indicate that galectin-3 causes a $Ca^{2+}$ influx, which is probably mediated by a PTX-sensitive G-protein coupled receptor(s).

Example 6

Figure 8:
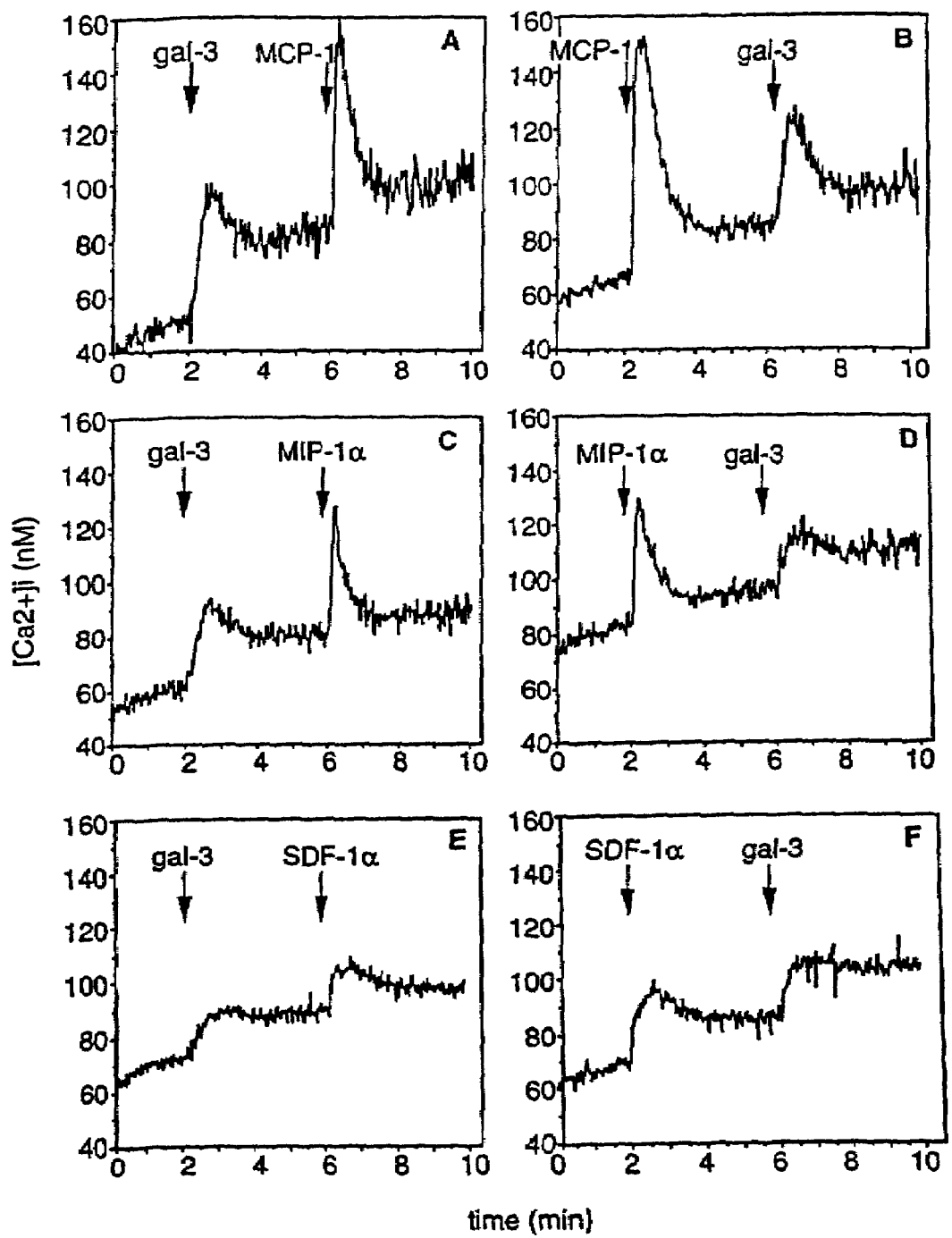
FIGS. 8A–F show the effect of chemokines on galectin-3-induced $Ca^{2+}$ mobilization in monocytes. Traces represent the average intracellular concentrations of $Ca^{2+}$ in the examined monocytes. Monocytes were stimulated first with galectin-3 and then with MCP-1 (A), MIP-1α (C), or SDF-1α (E), or first with MCP-1 (B), MIP-1α (D), or SDF-1α (F) and then with galectin-3. The final concentrations of galectin-3 and each chemokine in the cell suspensions were 1 μM and 100 ng/ml, respectively. The first and the second stimulants were added to the cell suspension at 2 and 6 min after the start of the measurement. Each figure shows representative data from 3 individual experiments using different donors.

Use of Known Chemokine Receptors on Monocytes by Galectin-3 to Induce $Ca^{2+}$ Influx Among various chemoattractants, the monocyte/macrophage-reactive chemokines including MCP-1, MIP-1α, and SDF-1α a are known to cause a $Ca^{2+}$ influx in the cells (Sozzani, et al., J. Immunol. 150:1544–53 (1993); Bizzari, et al., Blood 86:2388–94 (1995); Oberlin, et al., Nature 382: 833–35 (1996)) by binding to their receptors such as CCR2/9, CCR1/519, and CXCR-4, respectively, all of which are coupled with PTX-sensitive G-proteins (Baggiolini, Nature 392:565–68 (1998); Sallusto, et al., Immunol. Today 19:568–74 (1998); Zlotnik et al., Crit. Rev. Immunol. 19:1–47 (1999)). To determine the possibility that galectin-3 interacts with these receptors to transduce activation signal(s) into monocytes, $Ca^{2+}$ influx experiments were performed to study cross-desensitization. This method is known to be useful in identifying the usage of the chemoattractant receptors, although cross-desensitization occurs at multiple levels and can affect signals mediated by other receptors (Richardson, et al, J. Biol. Chem. 270:27829–33 (1995); Tomhave, et al., J. Immunol. 153:3267–75 (1994)). All of the chemokines (100 ng/ml) induced a $Ca^{2+}$ influx in human monocytes (FIG. 8A, C, E). Responses were desensitized by the pretreatment with the same but not other chemokines, consistent with previous results from other investigators (Sozzani, et al., J. Immunol. 150:1544–53 (1993); Bizzari, et al., Blood 86:2388–94 (1995); Oberlin, et al., Nature 382:833–35 (1996)). However, there was no cross-desensitization between galectin-3 and any of the above-mentioned monocyte-reactive chemokines (FIG. 8A–F). These results suggest that galectin-3 does not interact with any of these presently known chemokine receptors expressed on monocytes for signal transmission into the cell.

Example 7

Induction of Macrophages Migration by Galectin-3, but not MCP-1

Figure 9:
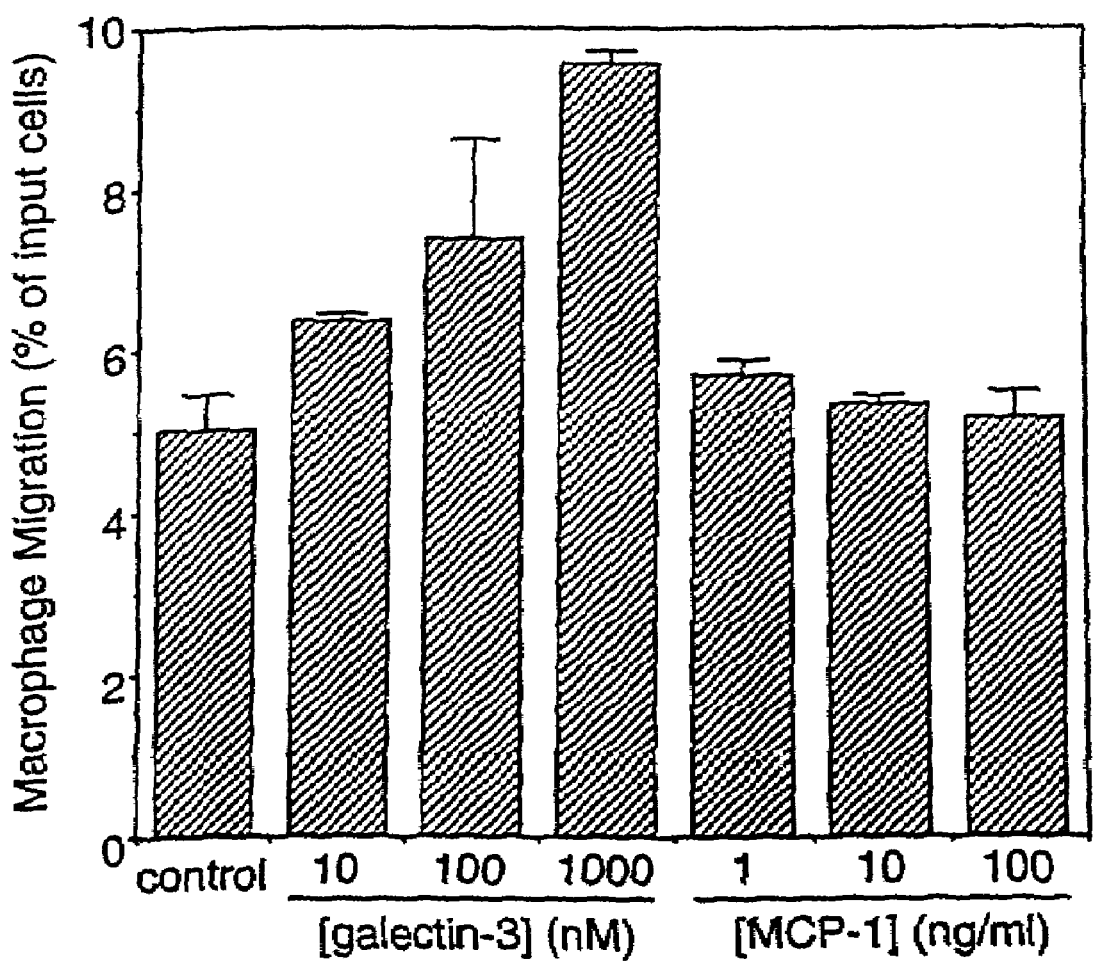
FIG. 9 is a bar graph illustrating the effect of galectin-3 and MCP-1 on the migration of cultured human peripheral blood macrophages in vitro. The assays were performed as described in FIG. 1. Data are the mean±SD of 3 individual experiments.
Figure 10:
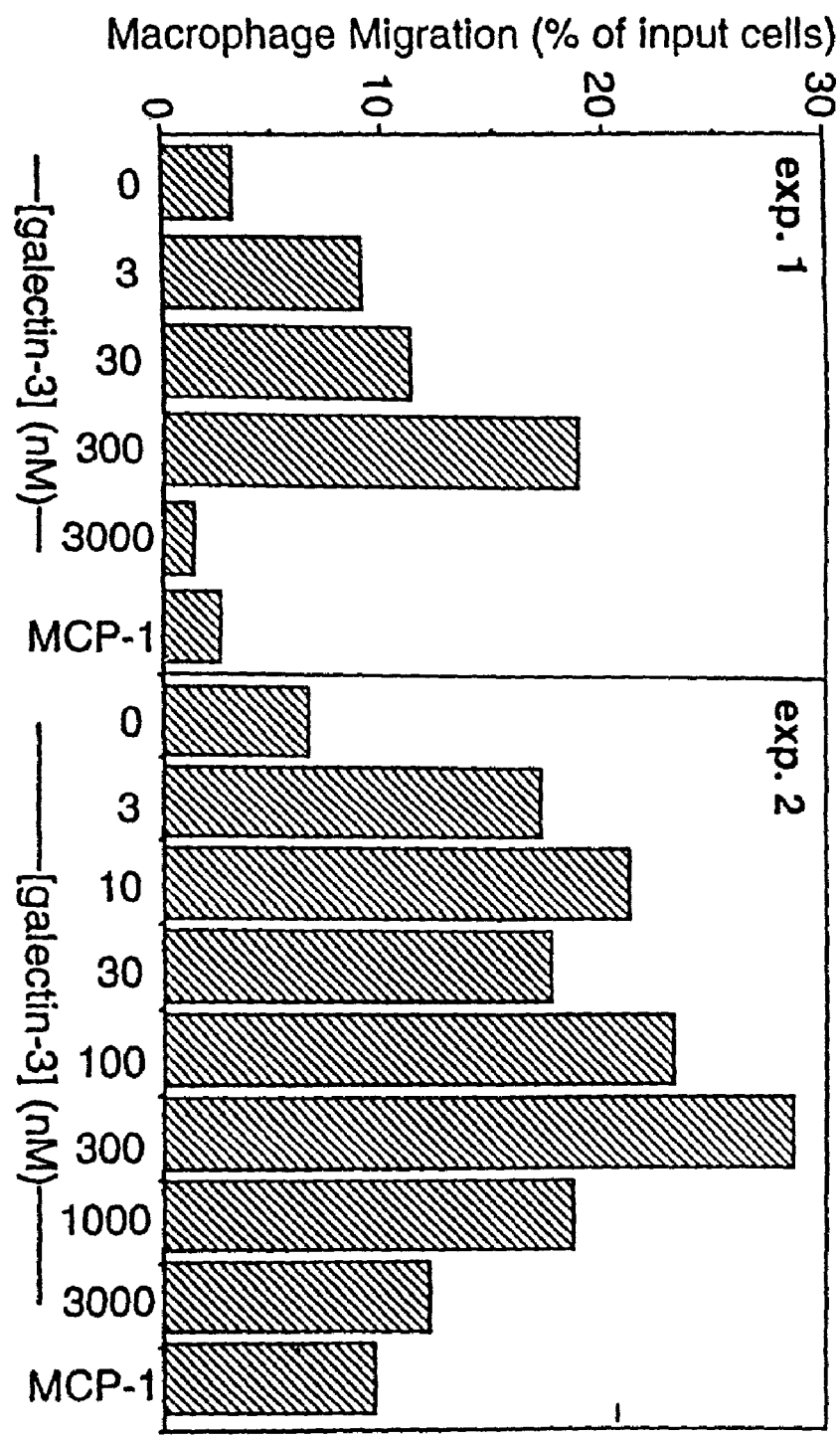
FIG. 10 depicts the effect of galectin-3 and MCP-1 on the migration of human alveolar macrophages in vitro. Alveolar macrophages obtained from bronchoalveolar lavage (BAL) fluid were used in a standard migration assay. The results from 2 separate experiments are shown.

Unlike monocytes, few chemokines have been shown to attract mature macrophages (Zlotnik et al., Crit. Rev. Immunol. 19:1–47 (1999)). To determine the effect of galectin-3 on mature macrophages, human macrophages obtained from culturing peripheral blood monocytes as well as alveolar macrophages were used. Cultured human macrophages do not express a detectable amount of CCR2 and do not respond to its ligand MCP-1 (Fantuzzi, et al., Blood 94:875–83 (1999)), which we also confirmed (FIG. 9). In contrast, galectin-3 induced macrophage migration in a dose-dependent manner, and 1 μM galectin-3 enhanced the migration by 190% over that induced by the control medium ($p<0.05$, n=3) (FIG. 9). Similarly, human alveolar macrophages migrated towards galectin-3 in two separate experiments (FIG. 10). In these experiments, bell-shaped dose-response curves were obtained, which is commonly observed for many chemokines. In contrast, MCP-1 had no effect (FIG. 10, exp. 1) or a negligible effect (FIG. 10, exp. 2) on macrophage migration. These results indicate that galectin-3 but not MCP-1 is a chemoattractant for macrophages. The results also corroborate the conclusion made above that the signaling pathway induced by galectin-3 is not mediated through CCR2.

Example 8

Galectin-3 Induced Monocyte Migration in vivo

The effect of galectin-3 on cell recruitment into mouse air pouches was examined to determine whether galectin-3 induces migration of cells in vivo. As shown in FIG. 11, galectin-3 increased the numbers of monocytes and neutrophils in the air pouch by 11.6 and 8.21 times, respectively, over those induced by vehicle (saline) only ($p<0.05$, $n=4$). In contrast, the numbers of lymphocytes and eosinophils were not augmented significantly by the treatment ($p=0.309$ and $0.112$, respectively). These results indicate that galectin-3 selectively recruits monocytes and neutrophils in vivo.

Example 9

Galectin-3 Induced Macrophage Migration in vivo

Figure 12:
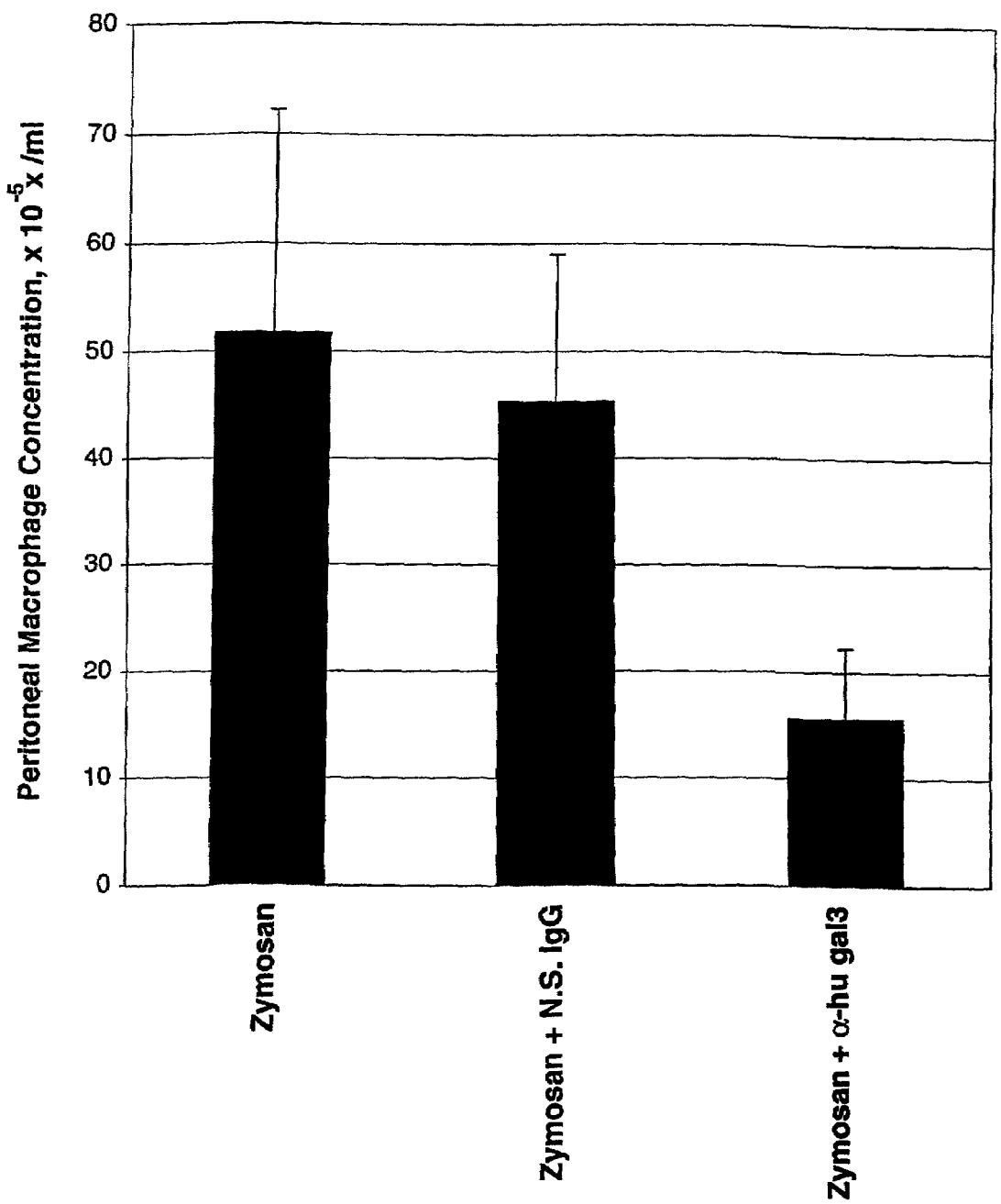
FIG. 12 shows that significantly fewer macrophages were recovered from the peritoneal cavity of mice treated with the anti-galectin-3 antibody (α-hu gal3) as compared to mice treated with control antibody (N.S. IgG).

Briefly, mice were treated either with mouse monoclonal anti-galectin-3 antibody (B2C10) or isotype-matched non-specific control antibody (300 μg/mouse) intraperitoneally. Thirty min after antibody treatment, zymosan (0.1 mg/g) was administered intraperitoneally. The following day, peritoneal lavage was performed with 3 ml of PBS and leukocytes contained in the recovered fluid were enumerated. As shown in FIG. 12, significantly fewer macrophages were recovered from the peritoneal cavity of mice treated with the anti-galectin-3 antibody (α-hu gal3) as compared to mice treated with control antibody (N.S. IgG). The results support a role for galectin-3 in regulation of macrophage infiltration during the inflammatory response, and are consistent with the previous finding that galectin-3 is a chemoattractant for monocytes/macrophages.

What is claimed is:

1. A method for modulating migration of a cell that expresses a galectin-3 receptor, said cell capable of having migration modulated by galectin-3, comprising contacting the cell with a migration-increasing or migration-decreasing amount of galectin-3.

2. A method for modulating monocyte, neutrophil, eosinophil, or macrophage migration comprising contacting a monocyte, neutrophil, eosinophil, or macrophage with a migration-increasing or migration-decreasing amount of galectin-3.

3. The method of claim 1 or 2, wherein the migration is stimulated.

4. The method of claim 1 or 2, wherein the migration is inhibited.

5. The method of claim 1 or 2, wherein the migration is modulated in an animal.

6. A method for increasing migration of monocytes, neutrophils, eosinophils, or macrophages to an inflammatory site comprising contacting the inflammatory site with a migration-increasing amount of galectin-3.

7. A method for increasing migration of monocytes, neutrophils, eosinophils, or macrophages to a site of infection comprising contacting the infection site with a migration-increasing amount of galectin-3.

8. A method for increasing migration of monocytes, neutrophils, eosinophils, or macrophages to a tumor comprising contacting the tumor with a migration-increasing amount of galectin-3.

9. A method for decreasing migration of monocytes, neutrophils, eosinophils, or macrophages to an inflammatory site comprising contacting the inflammatory site with a migration-decreasing amount of galectin-3.

10. A method for decreasing migration of monocytes, neutrophils, eosinophils, or macrophages to a site of infection comprising contacting the infection site with a migration-increasing amount of galectin-3.

11. A method for modulating migration of a cell that expresses a galectin-3 receptor comprising contacting the cell with a migration-increasing or migration-decreasing amount of a galectin-3 binding antibody.

12. A method for modulating monocyte, neutrophil, eosinophil, or macrophage migration comprising contacting a monocyte, neutrophil, eosinophil, or macrophage with a migration-increasing or migration-decreasing amount of a galectin-3 binding antibody.

13. The method of claim 11 or 12, wherein the migration is stimulated.

14. The method of claim 11 or 12 wherein the migration is inhibited.

15. The method of claim 11 or 12 wherein the galectin-3 binding antibody comprises a binding fragment of galectin-3 binding antibody.

16. The method of claim 11 or 12 wherein the migration is modulated in an animal.

17. A method for increasing migration of monocytes, neutrophils, eosinophils, or macrophages to an inflammatory site comprising contacting the inflammatory site with a migration-increasing amount of a galectin-3 binding antibody.

18. A method for increasing migration of monocytes, neutrophils, eosinophils, or macrophages to a site of infection comprising contacting the infection site with a migration-increasing amount of a galectin-3 binding antibody.

19. A method for increasing migration of monocytes, neutrophils, eosinophils, or macrophages to a tumor comprising contacting the tumor with a migration-increasing amount of a galectin-3 binding antibody.

20. A method for decreasing migration of monocytes, neutrophils, eosinophils, or macrophages to an inflammatory site comprising contacting the inflammatory site with a migration-decreasing amount of a galectin-3 binding antibody.

21. A method for increasing migration of monocytes, neutrophils, eosinophils, or macrophages to a site of infection comprising contacting the infection site with a migration-increasing amount of a galectin-3 binding antibody.

* * * * *